United States Patent [19]

Arndts et al.

[11] Patent Number: 5,643,919

[45] Date of Patent: Jul. 1, 1997

[54] ANELLATED DIHYDROPYRIDINES AND THE USE THEREOF FOR THE PRODUCTION OF PHARMACEUTICAL PREPARATION

[75] Inventors: Dietrich Arndts, Appenheim; Walter Lösel, Gau-Algesheim; Otto Roos, Schwabenheim, all of Germany

[73] Assignee: Boehringer Ingelheim KG, Ingelheim am Rhein, Germany

[21] Appl. No.: 475,154

[22] Filed: Jun. 7, 1995

Related U.S. Application Data

[63] Continuation of Ser. No. 249,822, May 26, 1994, abandoned.

[30] Foreign Application Priority Data

| Jun. 22, 1992 | [DE] | Germany | 42 20 369.4 |
| Jun. 22, 1992 | [DE] | Germany | 42 20 373.2 |
| Jun. 22, 1992 | [DE] | Germany | 42 20 312.0 |
| Jun. 22, 1993 | [DE] | Germany | 42 20 368.6 |
| Jun. 22, 1993 | [DE] | Germany | 42 20 345.7 |
| Jun. 22, 1993 | [DE] | Germany | 42 20 355.4 |
| Jun. 22, 1993 | [DE] | Germany | 42 20 319.8 |
| Jun. 22, 1993 | [DE] | Germany | 42 20 353.8 |

[51] Int. Cl.$^6$ ............. A61K 31/47; C07D 217/24; C07D 217/22; C07D 217/12
[52] U.S. Cl. ............. 514/292; 544/124; 544/363; 546/84; 546/90; 546/146; 514/235.2; 514/249
[58] Field of Search .......... 544/124; 546/84, 546/90, 146; 514/292, 235.2, 249

[56] References Cited

U.S. PATENT DOCUMENTS 4,322,418 3/1982 Losel .................. 424/248.57

FOREIGN PATENT DOCUMENTS 0288048 4/1988 European Pat. Off. .
3827727 2/1990 Germany .

OTHER PUBLICATIONS

Chemical Abstracts, 108:167455n, 1988.
Dautova, "Synthesis and Antiarrythmic and Anticoagulant . . . ", Khim.–Farm. Zh., 23(2), pp. 172–176, 1989.

*Primary Examiner*—C. Warren Ivy
*Assistant Examiner*—D. Margaret M. Mach
*Attorney, Agent, or Firm*—R. P. Raymond; M-E. M. Devlin; A. R. Stempel

[57] ABSTRACT

Compound of general formula I

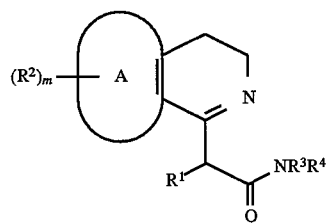

wherein
A is a benzo or thieno group;
$R_1$ is $(C_{4-6})$cycloalkyl, $(C_{4-6})$cycloalkyl-$(C_{1-5})$alkyl or

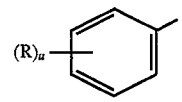

$R^2$, m, $R^3$, $R^4$, R and u are defined as in the specification, and pharmaceutical preparations containing this compound and the new pharmaceutical uses thereof.

7 Claims, No Drawings

ANELLATED DIHYDROPYRIDINES AND THE USE THEREOF FOR THE PRODUCTION OF PHARMACEUTICAL PREPARATION

This is a continuation of application Ser. No. 08/249,822 filed May 26, 1994 now abandoned.

The invention relates to anellated dihydropyridinoacetic acid derivatives, processes for preparing them and pharmaceutical compositions containing these compounds.

Dihydroisoquinolines are known from EP-A 37 934. The compounds mentioned therein have a cardiotonic activity and have an activity component which increases contractility and influences blood pressure. They have been proposed for improving circulation of the blood through the tissues and for improving the supply of oxygen to the tissues. These possible uses are based on the vascular activity of the compounds. EP-A 251 194 describes how carbocyclically and heterocyclically anellated dihydropyridines have a cardioprotective activity and constitute an entirely new type of Ca-antagonistic compounds.

The present invention relates to new carbocyclically and heterocyclically anellated dihydropyridines, and the pharmaceutical use of these compounds and new pharmaceutical uses for the dihydroisoquinolines known from EP-A-37 934. These new uses are based on their antiproliferative effect and their activity in the treatment of ulcerative colitis and Crohn's disease.

One aspect of the invention consists in the use of a compound of general formula I

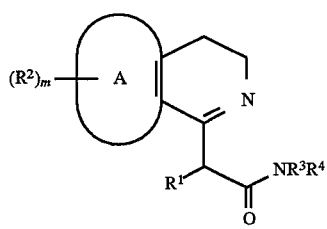

I wherein

A denotes a benzo, indolo or thieno group; wherein, if A is benzo, m is 2 or 3 (preferably 2, the two $R^2$ groups being in positions 6 and 7), and the substituents $R^2$ independently of each other may represent hydroxy, $(C_{1-4})$alkoxy, benzyloxy, halogen (F, Cl, Br, I), $(C_{1-4})$alkyl, methanesulphonyloxy or methanesulphonamido, or two adjacent substituents $R^2$ together represent —O—$CH_2$—O— or —O—$CH_2$—$CH_2$—O—; and if A is indolo or thieno, m is zero;

$R_1$ denotes $(C_{4-6})$cycloalkyl, $(C_{4-6})$cycloalkyl$(C_{1-5})$alkyl or

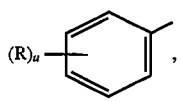

$R^3$ and $R^4$ independently of each other denote
(a) hydrogen,
(b) branched or unbranched $C_{3-6}$-alkenyl,
(c) branched or unbranched $C_{3-6}$-alkynyl or
(d) branched or unbranched $C_{1-12}$-alkyl, whilst the alkyl may be substituted by
hydroxy,
di$(C_{1-4})$alkylamino,
furyl,
pyridyl,
pyrrolidinyl, N-methylpyrrolidinyl,
morpholino,
indolyl,
nitrilo,
thienyl,
adamantyl,
cyclohexyl,
phenoxy,
naphthyloxy or phenyl, whilst this phenyl or the phenyl contained in the phenoxy group may be mono-, di- or trisubstituted by hydroxy, $(C_{1-4})$ alkoxy, benzyloxy, halogen (F, Cl, Br, I), $CF_3$, $N_3$, $(C_{1-4})$alkyl, adamantyl, —$SO_2NH_2$, —NHCOCH$_3$, —NHSO$_2$CH$_3$ or $CH_3SO_2O$— or by the bridge —O—$CH_2$—O—;

or $R^3$ denotes hydrogen and $R^4$ denotes cyclohexyl, phenyl, fluorophenyl, pyridyl or N-benzylpiperidyl;

or $R^3$ and $R^4$ together with the nitrogen atom to which they are bound represent
pyrrolidinyl,
piperidinyl,
morpholinyl, thiomorpholinyl, the group

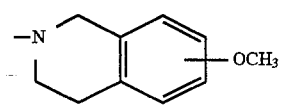

or piperazinyl, whilst the piperazinyl ring may optionally be N-substituted by methyl, unsubstituted phenyl, mono- or di$(C_{1-4})$ alkoxyphenyl, pyrimidinyl, phenyl$(C_{1-4})$alkyl or

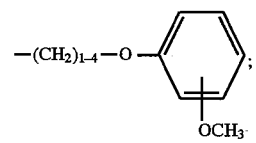

R denotes $C_{1-4}$-alkyl, hydroxy, —$N_3$, halogen (F, Cl, Br, I), $CF_3$, $C_{1-4}$-alkoxy or —COH and
u denotes 0, 1, 2 or 3;

A further aspect of the invention consists in the following new compounds: of general formula

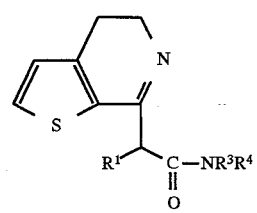

wherein $R^1$, $R^3$ and $R^4$ are as defined above; and new compounds of general formula I

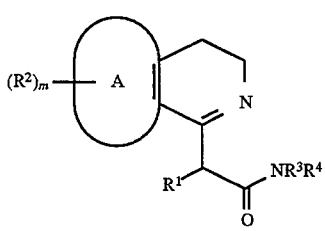

wherein

A denotes a benzo, indolo or thieno group; wherein, if A is benzo, m is 2 or 3 (preferably 2, the two $R^2$ groups being in positions 6 and 7), and the substituents $R^2$ independently of each other may represent hydroxy, $(C_{1-4})$alkoxy, benzyloxy, halogen (F, Cl, Br, I), $(C_{1-4})$ alkyl, methanesulphonyloxy or methanesulphonamido, or two adjacent substituents $R^2$ together represent —O—CH$_2$—O— or —O—CH$_2$—CH$_2$—O—; and if A is indolo or thieno, m is zero;

if A is indolo or thieno, m is zero;

$R_1$ denotes $(C_{4-6})$cycloalkyl, $(C_{4-6})$cycloalkyl$(C_{1-5})$alkyl or

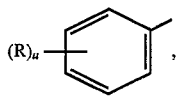

$R^3$ and $R^4$ independently of each other denote (a) hydrogen,
(b) branched or unbranched $C_{3-6}$-alkenyl,
(c) branched or unbranched $C_{3-6}$-alkynyl or
(d) branched or unbranched $C_{1-12}$-alkyl, whilst the alkyl may be substituted by
hydroxy,
$(C_{1-4})$alkoxy,
di$(C_{1-4})$alkylamino,
furyl,
pyridyl,
pyrrolidinyl, N-methylpyrrolidinyl,
morpholino,
indolyl,
nitrilo,
thienyl,
adamantyl,
cyclohexyl,
phenoxy,
naphthyloxy or phenyl, whilst this phenyl or the phenyl contained in the phenoxy group may be mono-, di- or trisubstituted by hydroxy, $(C_{1-4})$ alkoxy, benzyloxy, halogen (F, Cl, Br, I), CF$_3$, N$_3$, $(C_{1-4})$alkyl, adamantyl, —SO$_2$NH$_2$, —NHCOCH$_3$, —NHSO$_2$CH$_3$ or CH$_3$SO$_2$O— or by the bridge —O—CH$_2$—O—;

or $R^3$ denotes hydrogen and $R^4$ denotes cyclohexyl, phenyl, fluorophenyl, pyridyl or or $R^3$ and $R^4$ together with the nitrogen atom to which they are bound represent
pyrrolidinyl,
piperidinyl, morpholinyl, thiomorpholinyl, the group

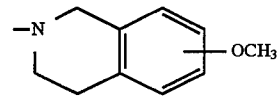

or piperazinyl, whilst the piperazinyl ring may optionally be N-substituted by methyl, unsubstituted phenyl, mono- or di$(C_{1-4})$ alkoxyphenyl, pyrimidinyl, phenyl$(C_{1-4})$alkyl or

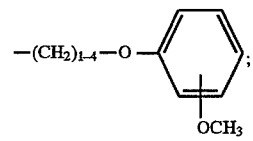

R denotes $C_{1-4}$-alkyl, hydroxy, —N$_3$, halogen (F, Cl, Br, I), CF$_3$, $C_{1-4}$-alkoxy or —COH and u denotes 0, 1, 2 or 3.

Another aspect of the invention consists in individual new compounds which come under the general definition of earlier patent applications. These compounds are contained, together with other compounds, in Tables 13 to 20, particularly Tables 14, 16 and 20. The following compounds of this group should be particularly mentioned:

New compounds of general formula I of the formula

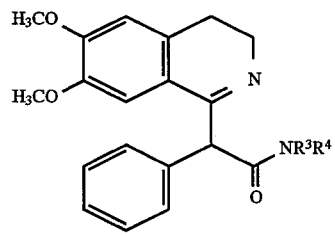

wherein NR$^3$R$^4$ has one of the following meanings

| | Structure |
|---|---|
| 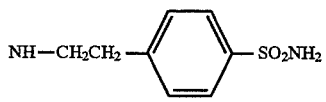 | I |
| 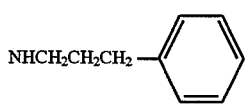 | I |

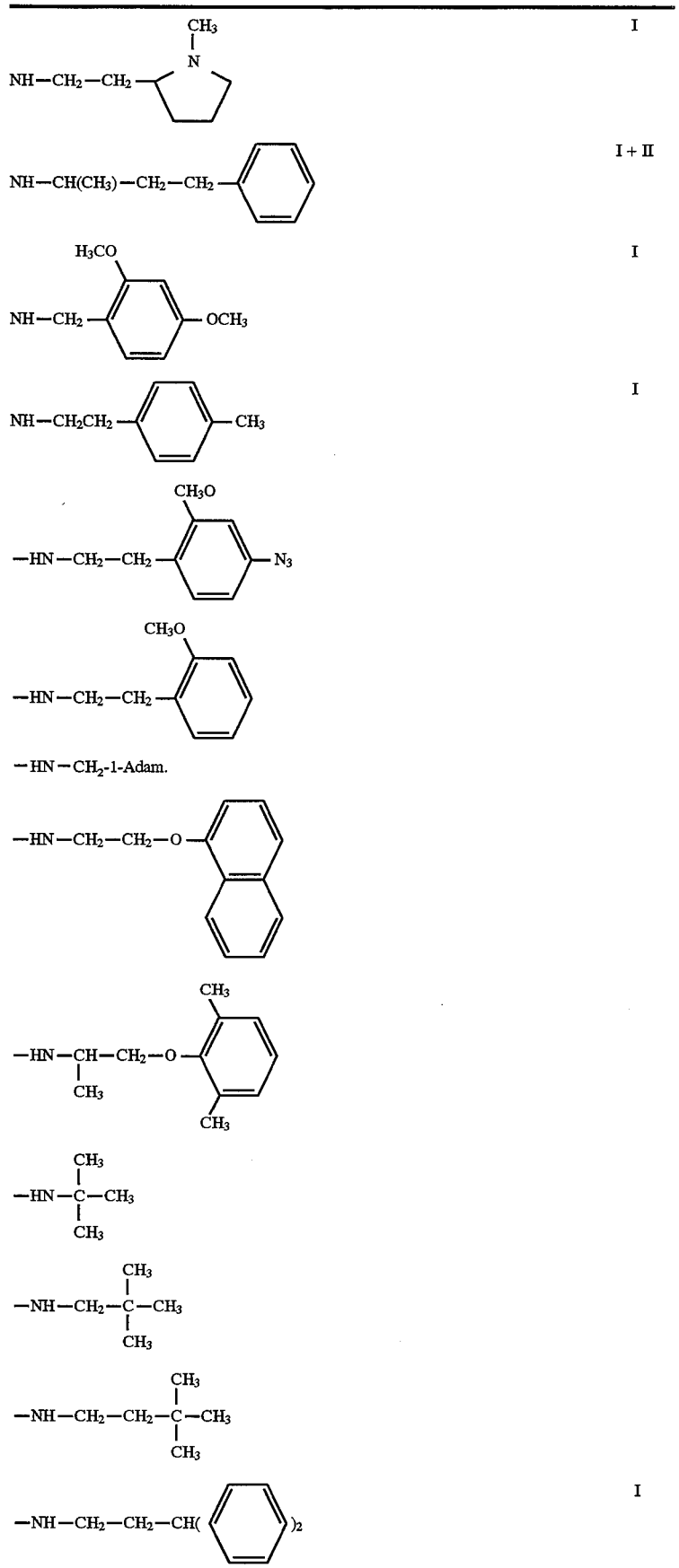

| | |
|---|---|
| 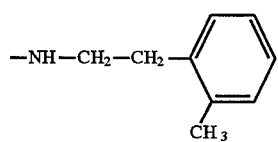 | I |
| 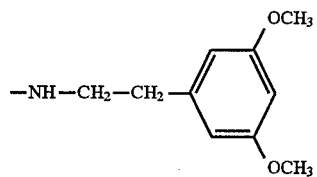 | I |
| 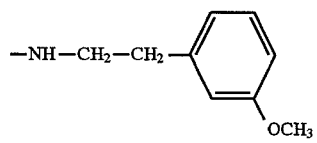 | I |
| 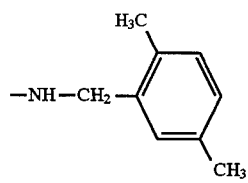 | I |
| X | Structure |
|---|---|
| 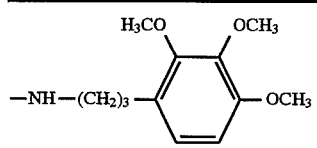 | I |
| 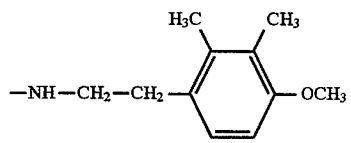 | II |
| 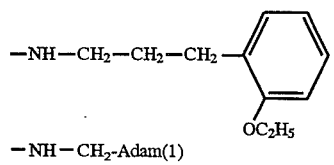 | I |
| —NH—CH$_2$-Adam(1) | II |
| 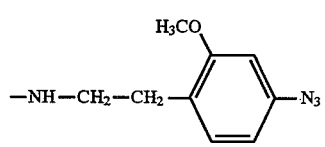 | I |
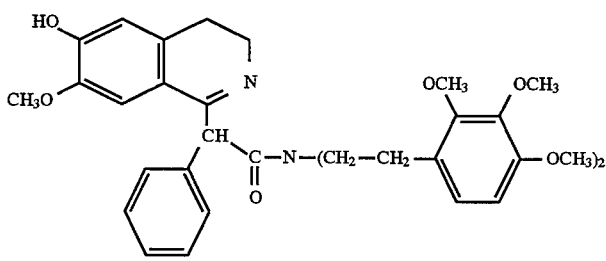

-continued

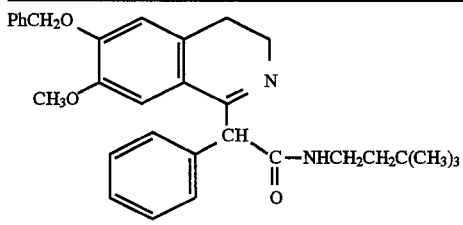

Compounds of formula I form tautomers of formula II

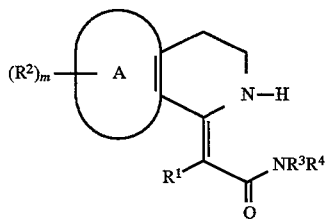

The tautomers can be separated by known methods, e.g. by column chromatography or selective reduction (NaBH$_4$ or catalytic reduction).

The compounds of formula II may be present in cis- and/or trans-form:

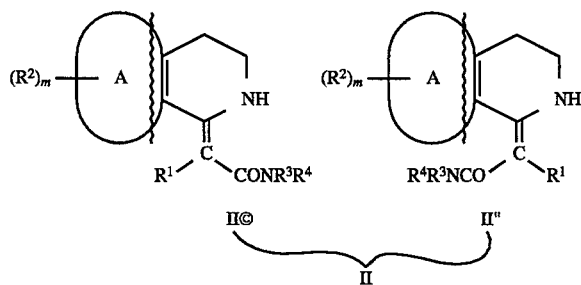

The invention also comprises the physiologically acceptable salts of the above new compounds with acids, bases and complexing agents.

The new compounds have valuable therapeutically useful properties. They can be used as cardioprotective agents, as cerebroprotective agents (particularly for the treatment of patients who have suffered a stroke or are in danger of suffering a stroke), and as agents for treating chronic inflammatory processes (e.g. bronchial asthma and arthritis). Furthermore, these compounds can be used as agents with an antiproliferative effect and as agents for treating ulcerative colitis and Crohn's disease.

In the definitions used in the text, the radicals and groups may be identical or different, i.e. if one of the abovementioned substituents occurs several times in one particular molecule, the meaning can be freely selected on each occasion within the scope of the range of definitions.

The term alkyl refers particularly to $C_{1-6}$-alkyl and $C_{1-4}$-alkyl radicals which may in turn be substituted or, as alkyl radicals, are part of a functional group such as alkoxy or alkylthio. The alkyl radicals include methyl, ethyl, n-propyl, isopropyl, n-butyl, sec.butyl, isobutyl, tert.butyl radicals and the various isomeric pentyl and hexyl radicals such as isopentyl, neopentyl, n-pentyl and the n-hexyl radical.

The above definition thus applies even when the alkyl radical is in turn substituted and/or is itself part of an alkoxyalkyl, alkoxycarbonyl, alkoxy, alkylthio, alkylsulphonyl, monoalkylamino, alkylmethyl, alkylthiomethyl, dialkylamino group or the alkyl radical is bound as a substituent to an aromatic heterocyclic or carbocyclic system.

The halogens are fluorine, chlorine, bromine and iodine, preferably fluorine, chlorine:and bromine and, to a lesser extent, iodine.

$C_{3-6}$-cycloalkyl means cyclopropane, cyclobutane, cyclopentane and cyclohexane. $C_{5-6}$-cycloalkenes are for example cyclopentene, cyclohexene and cyclohexadiene.

The $C_2$- and $C_3$-acyl radicals represent the acetyl and propionyl radicals.

$C_{3-6}$-alkynes are the isomeric hexynes, pentynes, butynes and propynes, preferably propargyl.

The $C_{3-6}$-alkenes are the isomeric hexenes, pentenes, butenes and propenes, preferably allyl.

Examples of unsaturated heterocycles include, inter alia: furan, pyran, pyrrole, pyrazole, imidazole, pyridine, pyrazine, pyrimidine, pyridazine, thiophene, thiazole, oxazole, 1,2,4-triazole, 1,2,3-triazole, 1,2,4-triazine, 1,3,5-triazine, indole.

Examples of 5- or 6-membered, wholly or partially saturated monocyclic heterocycles include inter alia:
imidazolidine, pyrazolidine, pyrrolidine, piperidine, piperazine, morpholine, thiomorpholine, tetrahydrofuran, tetrahydrothiophene, 1,4-dioxine, imidazoline, pyrazoline, pyrroline, etc.

A. Of the compounds of formula I wherein $R^1$ is ($C_{4-6}$) cycloalkyl or ($C_{4-6}$)cycloalkyl($C_{1-5}$)alkyl, the following may be mentioned as of particular interest:

Compounds wherein
$R^3$ and $R^4$ independently of each other denote (a) hydrogen, (b) $C_{1-8}$-alkyl, $C_{2-3}$-alkenyl or -alkynyl (wherein the alkyl may be substituted by hydroxy, ($C_{1-4}$)alkoxy, di($C_{1-4}$)alkylamino, furyl, pyrrolidinyl, morpholinyl, pyridinyl or the group

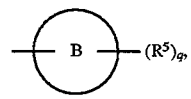

wherein B, $R^5$ and q are defined as hereinafter) (d) dimethylamino, (f) phenyl, (g) morpholinyl or (h) pyridyl, whilst $R^3$ and $R^4$ cannot simultaneously represent hydrogen, dimethylamino or di($C_{1-4}$) alkylaminomethyl;

or $R^3$ and $R^4$ together with the nitrogen atom to which they are bound denote a pyrrolidinyl, morpholinyl or piperazinyl group, whilst the piperazinyl ring may optionally be N-substituted by unsubstituted phenyl, mono- or di($C_{1-4}$)alkoxyphenyl, pyrimidinyl or phenyl ($C_{1-4}$)alkyl;

more particularly wherein $R^3$ and/or $R^4$ denotes unsubstituted phenyl, fluorophenyl, morpholino or 2- or 3-pyridyl;

wherein R³ and/or R⁴ denotes $(C_{1-4})$alkyl, preferably methyl or ethyl; or

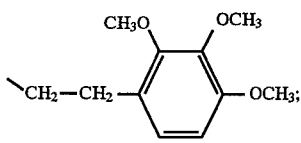

wherein R³ and/or R⁴ denotes ($C_2$ or $C_3$)alkyl, which is substituted by hydroxy, methoxy, dimethylamine, furyl, morpholino, pyrrolidinyl or pyridinyl;

wherein R³ is hydrogen.

Moreover, of these compounds (I), special mention should be made of those wherein R³ is hydrogen and R⁴ is a substituted alkyl of formula VII

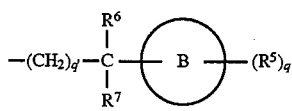

wherein q' is 0, 1 or 2;

R⁶ and R⁷ independently of each other denote hydrogen or $(C_{1-5})$alkyl or together with the carbon atom to which they are bound denote a 5- or 6-membered carbocycle;

B denotes phenyl or thienyl;

R⁵ denotes $(C_{1-4})$alkyl, halogen (F, Cl, Br, I), hydroxy, $(C_{1-4})$alkoxy, amino, thiomethyl, methanesulphonyloxy or methanesulphonamido, or two adjacent R⁵ substituents together denote —O—CH₂—O— or —O—CH₂—CH₂—O— and q' denotes 0, 1, 2 or 3, if B is phenyl, and q' denotes 0, 1, or 2 if B is thienyl;

more especially compounds wherein R⁵ denotes $(C_{1-4})$ alkyl, hydroxy, $(C_{1-4})$alkoxy, methanesulphonyloxy or methanesulphonamido, or two adjacent R⁵ substituents together denote —O—CH₂—O— or —O—CH₂—CH₂—O—;

wherein R⁵ represents hydroxy, $(C_{1-4})$alkoxy, methanesulphonyloxy or methanesulphonamido, or two adjacent R⁵ substituents together represent —O—CH₂—O— or —O—CH₂—CH₂—O—; particularly wherein R⁵ represents hydroxy, methoxy, methanesulphonyloxy or methanesulphonamido, or two adjacent R⁵ substituents together represent —O—CH₂—O—; particularly compounds wherein R⁵ is methoxy;

wherein q is zero;

wherein B is phenyl and q is two, preferably wherein the two R⁵ substituents are in positions 2 and 3.

Mention should also be made of compounds wherein R³ and R⁴ together with the nitrogen atom to which they are bound represent morpholino, pyrrolidinyl or piperazinyl (which is N-substituted by methoxyphenyl, phenethyl or 2-pyrimidinyl).

Of the above-mentioned groups of compounds the preferred ones are those wherein

R² represents hydroxy, $(C_{1-4})$alkoxy, methanesulphonyloxy or methanesulphonamido, or two adjacent R² substituents together represent —O—CH₂—O— or —O—CH₂—CH₂—O—; particularly wherein R² is methoxy.

B. Of the compounds of formula I wherein R¹ is

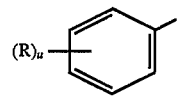

the compounds which may be mentioned as being of particular interest are those wherein R³ denotes hydrogen; and R⁴ denotes hydrogen, $C_{3-6}$-alkenyl; $C_{3-6}$-alkynyl; $C_{3-6}$-cycloalkyl; $C_{3-6}$-cycloalkenyl; straight-chained or branched $C_{1-6}$-alkyl, which may optionally be mono- or polysubstituted with the following substituents of groups a) to c), which may be identical or different:

a) halogen; cyano; hydroxy; mercapto; $C_{1-4}$-alkoxy; $C_{1-4}$-alkylthio; amino; mono-$C_{1-4}$-alkylamino; di-$C_{1-4}$-alkylamino (wherein the alkyl radicals may be identical or different), phenoxy (wherein the phenyl group may be substituted as in (b)), b) phenyl; optionally mono- or polysubstituted (with identical or different substituents) by the groups halogen, trifluoromethyl, $C_{1-4}$-alkoxy, hydroxy, mercapto, $C_{1-4}$-alkylthio, $C_{1-4}$-alkyl, amino, mono-$C_{1-4}$-alkylamino, di-$C_{1-4}$-alkylamino (wherein the alkyl groups may be identical or different), $C_{2-3}$-acylamino, $C_{2-3}$-acyloxy and the —O—CH₂—O— or —O—(CH₂)₂—O— group vitally bound to the phenyl system, c) a 5- or 6-membered saturated or wholly or partially unsaturated monocyclic heterocycle having up to 3 heteroatoms selected from the group comprising N, O and S; and as a bicyclic heterocycle indole (whilst the above-mentioned heterocycles may be mono- or polysubstituted by $C_{1-4}$-alkyl), $C_{3-6}$-cycloalkyl; $C_5$- or $C_6$-cycloalkenyl; $C_{2-3}$-acyl; $C_{1-4}$-alkylsulphonyl; or phenyl (which may in turn be substituted up to three times as described under b);

or R³ is hydrogen and R⁴ is phenyl which may be substituted as specified under b) above;

R₃ and R₄ independently of each other denote $C_{1-4}$-alkyl, which may optionally be phenyl-substituted, whilst the phenyl substituent may in turn be substituted as under b) hereinbefore; or R³ and R⁴ together with the nitrogen atom to which they are bound denote a wholly or partially saturated heterocyclic 5- or 6-membered ring (which may also contain up to two further heteroatoms selected from the group N, O, S), whilst the heterocyclic group thus obtained may be substituted by $C_{1-4}$-alkyl, hydroxy, phenyl or benzyl (whilst this phenyl group or the phenyl group of the benzyl group is substituted as under b) hereinbefore).

Within the description of general formula I is included in particular 3,4-dihydroisoquinoline derivatives wherein NR³R⁴ is

13

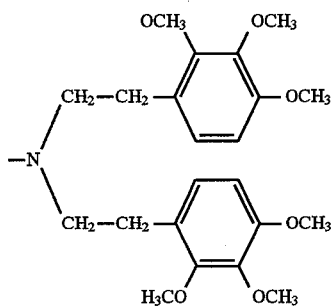

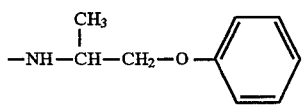

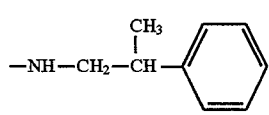

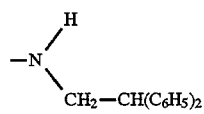

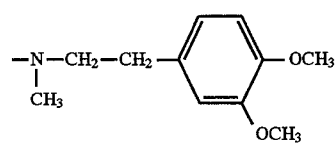

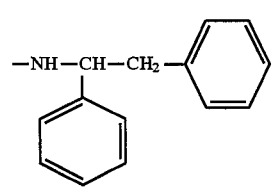

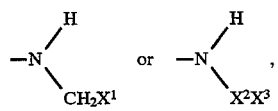

wherein $X^1$ represents phenyl mono- or disubstituted by trifluoromethyl or ethoxy, phenyl substituted by methoxy and fluorine or 2-methoxyphenyl, $X^2$ is —CH$_2$—CH$_2$— or —CH$_2$—CH(CH$_3$)—, and $X^3$ is 2,3,4-trimethoxyphenyl, 2,3-dimethoxyphenyl, 2,6-dimethoxyphenyl, 3,6-dimethoxyphenyl, thienyl, phenyl mono- or disubstituted by trifluoromethyl or ethoxy, or phenyl substituted by methoxy and fluorine, or the pharmaceutically acceptable salts thereof.

The preferred compounds (I) are those wherein

14

$NR^3R^4$ is

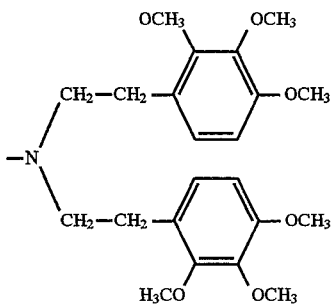

Carbocyclically and heterocyclically anellated dihydropyridines of the formula

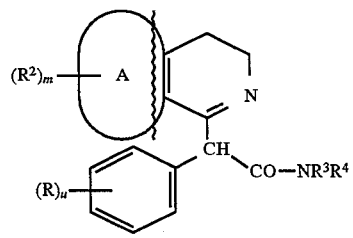

and the tautomeric forms thereof, wherein $R^3$ denotes hydrogen and $R^4$ denotes hydrogen; straight-chained or branched unsubstituted $C_{1-5}$-alkyl; allyl; propargyl; $C_{3-6}$-cycloalkyl; 3-chlorophenyl; 2-methyl-3-chlorophenyl; or $C_{1-3}$-alkyl, which is monosubstituted with one of the substituents of groups d) to f) listed below;

d) cyano, hydroxy, methoxy, dimethylamino e) phenyl, 3,4-methylenedioxyphenyl, phenyl substituted by one, two or 3 methoxy groups, 3-hydroxy-4-methoxyphenyl, f) morpholino, pyridin-2-yl, indol-3-yl, furan-2-yl, thiophen-2-yl, pyridin-3-yl, pyridin-4-yl;

$R^3$ and $R^4$ independently of each other denote methyl; ethyl; 3-cyanopropyl; benzyl; or 3,4,5-trimethoxyphenethyl or $R^3$ and $R^4$ together with the nitrogen atom to which they are bound represent morpholine; thiomorpholine; pyrrolidine; piperazine; 4-methylpiperazine; 4-benzylpiperazine or 4-(2-methoxyphenyl)piperazine; and A represents the anellated ring systems

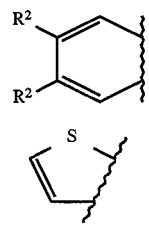

are preferred.

The phenyl group of the compound of general formula I may contain 1, 2 or 3 R substituents. These R substituents may be identical or different from one another. Preferably R is $C_{1-4}$-alkyl (preferably methyl), halogen (preferably fluorine, chlorine or bromine) or $CF_3$.

C. Of the compounds of formula I wherein $R^1$ is unsubstituted phenyl, particular mention may be made of those compounds wherein $R^3$ is hydrogen and $R^4$ is hydrogen, $C_{3-6}$-alkenyl; $C_{3-6}$-alkynyl-, $C_{3-6}$-cycloalkyl; $C_{3-6}$-alkyl anellated with a benzo group; $C_{3-6}$-cycloalkenyl; straight-chained or branched $C_{1-10}$-alkyl, which may optionally be mono- or polysubstituted with the following substituents of groups a) to c), which may be identical or different:

a) cyano; hydroxy; $C_{1-4}$-alkoxy; $C_{1-4}$-alkylthio; $C_{1-4}$-alkyloxycarbonyl; amino; mono-$C_{1-4}$-alkylamino; di-$C_{1-4}$-alkylamino (wherein the alkyl radicals may be identical or different), phenoxy (wherein the phenyl group may be substituted as under (b); naphthoxy;

b) phenyl; optionally mono-, di- or trisubstituted (with identical or different substituents) by the groups halogen, trifluoromethyl, $C_{1-4}$-alkoxy, hydroxy, mercapto, $C_{1-4}$-alkylthio, $C_{1-4}$-alkyl, azido, amino, mono-$C_{1-4}$-alkylamino, di-$C_{1-4}$-alkylamino (wherein the alkyl groups may be identical or different), $C_{2-3}$-acylamino, $C_{2-3}$-acyloxy and the group —O—CH$_2$—O— or —O—(CH$_2$)$_2$—O— vicinally bound to the phenyl system;

c) a 5- or 6-membered saturated or wholly or partially unsaturated monocyclic heterocycle having up to 3 heteroatoms from the group comprising N, O and S; and as a bicyclic heterocycle indole (whilst the above-mentioned heterocycles may be mono- or polysubstituted by $C_{1-4}$-alkyl) $C_{3-10}$-cycloalkyl (optionally bridged cycloalkyl); $C_5$- or $C_6$-cycloalkenyl; $C_{2-3}$-acyl; $C_{1-4}$-alkylsulphonyl;

or $R^4$ is phenyl which may be substituted as specified under (b) hereinbefore;

$R^3$ and $R^4$ independently of each other are each defined as for $R^4$ above, and preferably represent $C_{1-6}$-alkyl, which may optionally be phenyl-substituted, whilst the phenyl substituent may in turn be substituted as under b) hereinbefore; or $R^3$ and $R^4$ together with the nitrogen atom to which they are bound represent a wholly or partially saturated heterocyclic 5- or 6-membered ring (which may also contain up to 2 further heteroatoms selected from the group comprising N, O and S), whilst the heterocyclic group thus obtained may be substituted by $C_{1-4}$-alkyl, hydroxy or (CH$_2$)$_q$·$R^8$ (where q"=0,1,2,3 or 4); and $R^8$ denotes a phenyl radical or phenoxy radical wherein, if desired, the phenyl group is substituted as under b) hereinbefore, or $R^8$ denotes naphthoxy;

A denotes the anellated ring systems

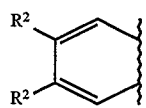

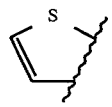

wherein $R^2$ is as hereinbefore defined, more particularly wherein $R^3$ is hydrogen and $R^4$ is hydrogen; $C_{3-6}$-alkenyl; $C_{3-6}$-alkynyl; $C_{3-6}$-cycloalkyl; $C_{3-6}$-cycloalkenyl; straight-chained or branched $C_{1-6}$-alkyl which may optionally be mono- or polysubstituted with the following substituents of groups a) to c), which may be identical or different:

a) halogen; cyano; hydroxy; mercapto; $C_{1-4}$-alkoxy; $C_{1-4}$-alkylthio; amino; mono-$C_{1-4}$-alkylamino; di-$C_{1-4}$-alkylamino (wherein the alkyl radicals may be identical or different), phenoxy (wherein the phenyl group may be substituted as under (b), b) phenyl; optionally mono- or polysubstituted (with identical or different substituents) by the groups halogen, trifluoromethyl, $C_{1-4}$-alkoxy, hydroxy, mercapto, $C_{1-4}$-alkylthio, $C_{1-4}$-alkyl, amino, mono-$C_{1-4}$-alkylamino, di-$C_{1-4}$-alkylamino (wherein the alkyl groups may be identical or different), $C_{2-3}$-acylamino,-$C_{2-3}$-acyloxy and the group —O—CH$_2$—O— or —O—(CH$_2$)$_2$—O— vicinally bound to the phenyl system c) a 5- or 6-membered saturated or wholly or partially unsaturated monocyclic heterocycle having up to 3 heteroatoms from the group N, O, S; and as a bicyclic heterocycle indole (whilst the above-mentioned heterocycles may be mono- or polysubstituted by $C_{1-4}$-alkyl), $C_{3-6}$-cycloalkyl; $C_5$- or $C_6$-cycloalkenyl; $C_{2-3}$-acyl; $C_{1-4}$-alkylsulphonyl; or phenyl (which may in turn be substituted up to three times as described under b);

$R^3$ is hydrogen and $R^4$ is phenyl which may be substituted as specified under (b) hereinbefore;

$R^3$ and $R^4$ independently of each other denote $C_{1-4}$-alkyl, which may optionally be phenyl-substituted, whilst the phenyl substituent may in turn be substituted as under b) hereinbefore; or $R^3$ and $R^4$ together with the nitrogen atom to which they are bound denote a wholly or partially saturated, heterocyclic 5- or 6-membered ring (which may also contain up to 2 further heteroatoms from the group N, O, S), whilst the resulting heterocycle may be substituted by $C_{1-4}$-alkyl, hydroxy or (CH$_2$)$_{q''}$—$R^8$ (wherein q"=0 or 1) and $R^8$ denotes a phenyl radical which may optionally be substituted as under b) hereinbefore;

A denotes the anellated ring systems

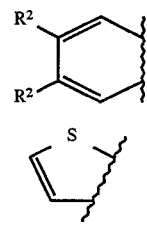

wherein $R^2$ is as hereinbefore defined.

General formula I as described covers, in particular, 3,4-dihydroisoquinoline derivatives of the general formula

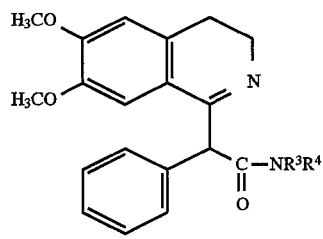

wherein NR³R⁴ represents

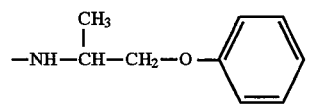

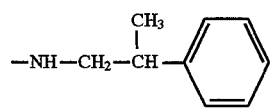

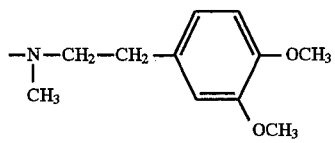

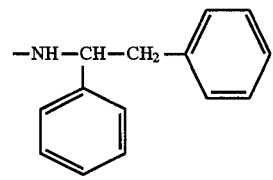

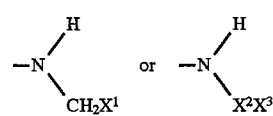

wherein

X¹ denotes phenyl which is mono- or disubstituted by trifluoromethyl or ethoxy, phenyl which is substituted by methoxy and fluorine, or 2-methoxyphenyl, X² denotes —CH₂—CH₂— or —CH₂CH(CH₃)—, and X³ denotes 2,3,4-trimethoxyphenyl, 2,3-dimethoxyphenyl, 2,6-dimethoxyphenyl, 3,6-dimethoxyphenyl, thienyl, phenyl which is mono- or disubstituted by trifluoromethyl or ethoxy, or phenyl substituted by methoxy and fluorine, or the pharmaceutically acceptable salts thereof.

Particularly preferred compounds are those wherein NR³R⁴ denotes

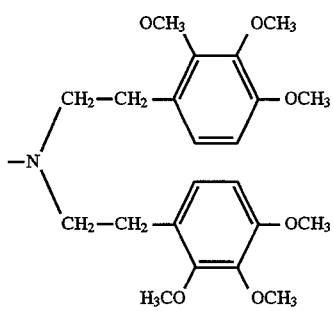

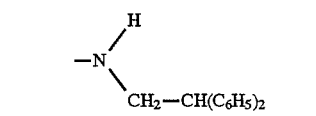

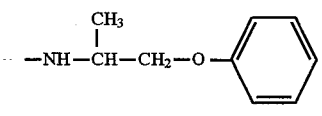

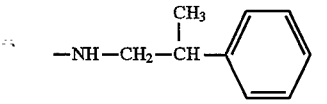

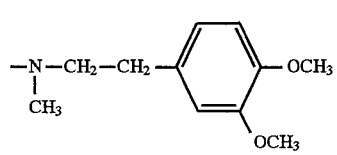

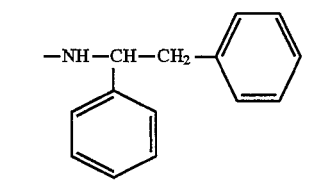

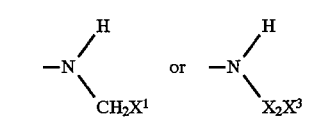

wherein

X¹ is 2-methoxyphenyl, which may additionally be substituted by fluoro,

X² is —CH₂—CH₂— and

X³ is 2,3,4-trimethoxyphenyl, 2,3-dimethoxyphenyl, 2,6-dimethoxyphenyl, 3,6-dimethoxyphenyl, 2- or 3-thienyl, phenyl substituted by trifluoromethyl or ethoxy, or phenyl substituted by methoxy and fluorine.

Particular mention should be made of compounds of the formula

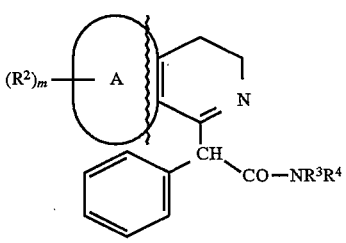

and the tautomeric forms thereof wherein

R³ is hydrogen and

R⁴ is hydrogen; straight-chained or branched unsubstituted $C_{1-5}$-alkyl; allyl; propargyl; $C_{3-6}$-cycloalkyl; 3-chlorophenyl; 2-methyl-3-chlorophenyl; or $C_{1-3}$-alkyl, which is monosubstituted with one of the substituents of groups d) to f) listed hereinafter;

d) cyano, hydroxy, methoxy, dimethylamino e) phenyl, 3,4-methylenedioxyphenyl, phenyl substituted by one, two or 3 methoxy groups, 3-hydroxy-4-methoxyphenyl, f) morpholino, pyridin-2-yl, indol-3-yl, furan-2-yl, thiophen-2-yl, pyridin-3-yl, pyridin-4-yl R³ and R⁴ independently of each other denote methyl; ethyl; 3-cyanopropyl; benzyl; or 3,4,5-trimethoxyphenethyl or R³ and R⁴ together with the nitrogen atom to which they are bound denote morpholine; thiomorpholine; pyrrolidine; piperazine; 4-methylpiperazine; 4-benzylpiperazine; or 4-(2-methoxyphenyl) piperazine; and

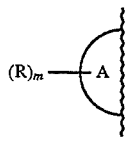

denotes the anellated ring systems

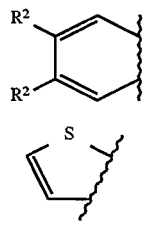

wherein
R² is as hereinbefore defined.

The compounds of formula I may be prepared by methods known per se, preferably according to the method described in German Patent Application P 37 18 570.5, EP 358 957, EP 37 934 and EP 251 794.

In the presence of a condensing agent a malonic acid amide of general formula IV

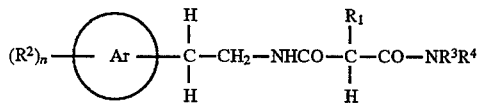

wherein R¹, R², R³, R⁴ and m are as hereinbefore defined and Ar denotes phenyl or 2- or 3-thienyl, may be cyclised into the corresponding compounds.

Suitable condensing agents for this process include strong Lewis acids such as phosphorusoxychloride, phosphoruspentachloride, phosphorustrichloride, phosphoruspentoxide, titanium tetrachloride, boron trifluoride, tin tetrachloride, and also inorganic acids such as polyphosphoric acid, sulphuric acid, fluorosulphonic acid and hydrofluoric acid, or mixtures of condensing agents such as a mixture of phosphorusoxychloride and phosphoruspentachloride, or a mixture of phosphoruspentoxide and $(C_{1-4})$alkylsulphonic acid, e.g. with a $P_2O_5$-content of about 10% by weight.

The cyclisation may be carried out in the presence or absence of a solvent. All inert solvents are suitable provided that they have sufficient solubility for the reactants and a high enough boiling point, e.g. benzene, alkylbenzenes (e.g. toluene, xylene), chlorobenzenes, chloroform, acetonitrile and decalin. According to a preferred alternative embodiment of the process the condensing agent, e.g. phosphorusoxychloride or a $(C_{1-4})$alkylsulphonic acid/phosphoruspentoxide mixture is used without the addition of solvents.

Preferably, the cyclisation is carried out using phosphorusoxychloride or, in difficult cases, with a mixture of phosphoruspentoxide and $(C_{1-4})$alkylsulphonic acid (preferably methanesulphonic acid). The reaction may be carried out within a wide temperature range, preferably with warming or heating to 50° C. up to about the boiling point of the reaction mixture.

The reaction time required will range from 2 to 15 hours depending on the starting compound of formula IV.

The compounds of formula I are bases and may be converted in the usual way with organic or inorganic acids and salt-forming agents and complexing agents into any desired physiologically acceptable adducts (salts).

Examples of acids suitable for salt formation include hydrochloric acid, hydrobromic acid, hydriodic acid, hydrofluoric acid, sulphuric acid, phosphoric acid, nitric acid, acetic acid, propionic acid, butyric acid, caproic acid, valetic acid, oxalic acid, malonic acid, succinic acid, maleic acid, fumaric acid, lactic acid, tartaric acid, citric acid, malic acid, benzoic acid, p-hydroxybenzoic acid, phthalic acid, cinnamic acid, salicylic acid, ascorbic acid, methanesulphonic acid and the like.

The compounds may be given orally, parenterally or topically. The desired therapeutic dose depends on the indication and form of preparation and can be determined experimentally. Suitable forms include, for example, tablets, capsules, suppositories, solutions, syrups, emulsions, aerosols or dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release, such as carboxypolymethylene, carboxymethylcellulose, cellulose acetate phthalate or polyvinylacetate. The tablets may also consist of several layers.

Coated tablets may be produced analogously by coating cores made in the same way as the tablets with substances conventionally used for tablet coatings, e.g. collidone or shellack, gum arabic, talc, titanium dioxide or sugar. In order to obtain delayed release or avoid incompatibilities, the core may also consist of several layers. Similarly, the tablet coating may consist of several layers to achieve delayed release, whilst the excipients mentioned for the tablets may be used.

Syrups containing the active substances or combinations of active substances according to the invention additionally contain a sweetener such as saccharin, cyclamate, glycerol or sugar as well as a flavour enhancer, e.g. a flayouting such as vanillin or orange extract. They may also contain suspension adjuvants or thickeners such as sodium carboxymethylcellulose, wetting agents, e.g. condensation products of fatty alcohols with ethylene oxide or preservatives such as p-hydroxybenzoates.

Injectable solutions are produced in the usual way, e.g. by adding preservatives such as p-hydroxybenzoates or stabilisers such as alkali metal salts of ethylene diamine tetraacetic acid, and are then transferred into injection vials or ampoules.

Capsules containing one or more active substances or combinations of active substances may be prepared for example by mixing the active substances with inert carriers such as lactose or sorbitol and encapsulating them in gelatine capsules.

Suitable suppositories may be produced for example by mixing with carriers provided for this purpose, such as neutral fats or polyethyleneglycol or derivatives thereof.

The compounds may be given both enterally and parenterally. The proposed dose for oral administration is 0.1 to 500 mg of active substance per dose, and for intravenous use 0.05 to 150 mg per dose. The desired therapeutic dose depends on the indication and form of preparation and can be determined experimentally.

The pharmaceutical compositions are suitable for oral or parenteral and possibly topical use. The pharmaceutical forms are predominantly plain or coated tablets, ampoules and syrups. The individual dose of these preparations is between 1.0 and 200 mg, preferably 20 to 50 mg per 75 kg of body weight. Depending on the severity of the case, 1 to 3 single doses are generally administered per day.

The Examples which follow are intended to illustrate the invention:

EXAMPLE 1

3,4-Dihydro-1-benzyl-6,7-dimethoxy-α-[di-2-(2,3,4-trimethoxyphenyl)ethyl]aminocarbonyl-isoquinolinehydrochloride

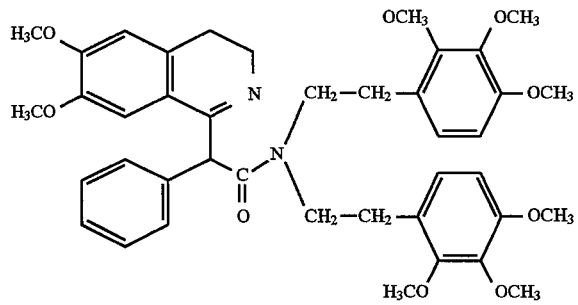

a) 2-(3,4-Dimethoxyphenyl)ethylaminocarbonyl-phenylacetic acid-N,N-di-[2-(2,3,4-trimethoxyphenyl)ethyl] amide To a solution of 18.0 g (52.4 mmol) of monoethylphenylmalonate-2-(3,4-dimethoxyphenyl) ethylamide in 150 ml of anhydrous dimethylformamide are added, at ambient temperature 9.0 g (55.5 mmol) of N,N'-carbonyldiimidazole in batches. After 30 minutes 18.0 g (44.3 mmol) of di-[2-(2,3,4-trimethoxyphenyl)ethyl]amine are added and the mixture is stirred for 30 minutes. Then the solvent is distilled off in vacuo, the residue is taken up in 1.5 liters of $CH_2Cl_2$ and extracted twice with 250 ml of water and 200 ml of 1N HCl, one after the other. The organic phase is evaporated down after drying over $Na_2SO_4$ and, after purification over a silica gel column (eluant: $CH_2Cl_2$/MeOH 100:2) the residue is crystallised from ethyl acetate/ether. Yield: 35.5 g b) 35.0 g (47.5 mmol) of amide (from step a) and 15 ml (164 mmol) of phosphorusoxychloride are heated to boiling for 30 minutes in 150 ml of anhydrous acetonitrile. After the reaction has ended (monitored by thin layer chromatography) the solvent and any unused phosphorusoxychloride are distilled off in vacuo. The residue is mixed with ice water, made alkaline with soda solution and extracted in batches with about 1 liter of $CH_2Cl_2$. The organic phase is washed with water, dried over $Na_2SO_4$ and evaporated down. The residue is purified twice over a silica gel column (1st eluant: $CH_2Cl_2$:MeOH 100:2→100:4 rising; 2nd eluant: $CH_2Cl_2$/ethyl acetate 1:1).

The hydrochloride is formed from the purified product (6.5 g) by dissolving in about 50 ml of ethanol and adding alcoholic hydrochloric acid. After evaporation and drying under a high vacuum at 50° C. 11.5 g of the desired product remain. (M.p.56°–64° C., amorphous)

EXAMPLE 2

2-Phenylmalonic acid-N-(2-(3,4-dimethoxyphenyl) ethyl)N', N'-di-(2-(2-fluorophenyl)ethyl)-diamide To a solution of 17.2 g (0.05 mol) of phenylmalonic acid N-(2-(3,4-dimethoxyphenyl)ethyl)-monoamide in 200 ml of anhydrous $CH_2Cl_2$, 8.1 g (0.05 mol) of N,N'-carbonyldiimidazole are added in batches at ambient temperature and with stirring. After about 30 minutes a suspension consisting of 14.9 g (0.05 mol) of di-(2-(2-fluorophenyl)ethyl)amine-hydrochloride and 5.1 g=6.4 ml (0.05 mol) of triethylamine in 100 ml of anhydrous $CH_2Cl_2$ is stirred into the reaction mixture. After 15 hours' stirring, 200 ml of water are added, the mixture is acidified with dilute hydrochloric acid, the organic phase is separated off and the aqueous phase is extracted 3 times with 100 ml of $CH_2Cl_2$. The combined organic phases are dried over $Na_2SO_4$ and evaporated down.

R,S (3,4-Dihydro-6,7-dimethoxyisoquinolin-1-yl)-2-phenyl N,N-di-(2-(2-fluorophenyl)ethyl-acetamide-oxalate A mixture of 29.8 g (0.049 mol) of amide, 150 ml of anhydrous $CH_2Cl_2$ and 17.5 g=9.4 ml (0.10 mol) of $POCl_3$ is refluxed for 10 hours. After the reaction has ended (TLC monitoring) the mixture is stirred into a combination of 400 ml of ice water and 200 ml of $CH_2Cl_2$. Then it is neutralised with a saturated soda solution, the organic phase is separated off, the aqueous phase is extracted 3 times with 100 ml of $CH_2Cl_2$. The combined phases are dried over $Na_2SO_4$ and evaporated down in vacuo. The residue is purified over silicic acid (eluant: $CH_2Cl_2$=methanol=100:2) and then dissolved in a little ethanol and converted into the oxalate by adding a stoichiometric quantity of an alcoholic oxalic acid solution. The oxalate is also crystallised by the addition of ether. M.p.: 144°–146° C.

EXAMPLE 3

(R,S)-(3,4-Dihydro-6,7-dimethoxyisoquinolin-1-yl)-
2-(4-methoxyphenyl)-N,N-di(2-(2,3,4-
trimethoxyphenyl)ethyl)acetamide-oxalate Ingredients:
5 g (6.57 mMol) of 4-methoxyphenylmalonic acid-N-(2-(3,4-dimethoxyphenyl)ethyl)-N'-(2-(2,3,4-trimethoxyphenyl)-ethyl-diamide ("diamide") 18 ml of acetonitrile, 3.02 g (19.7 mMol) of phosphorusoxychloride, 600 mg (6.66 mMol) of oxalic acid, anhydrous, 200 ml of ether
Method:

The reaction mixture of the "diamide", acetonitrile and phosphorusoxychloride is refluxed for 1 hour under protective $N_2$. After cooling with ice water it is diluted with 100 ml of ethyl acetate and then washed twice each with ice water, 50 ml of saturated $NaHCO_3$ solution, water and saturated NaCl solution. The organic phase is dried over $MgSO_4$ and poured, with stirring, into a solution of 706 mg (7.84 mMol) of anhydrous oxalic acid in 200 ml of absolute ether.

The reaction product was initially precipitated as an oil as the oxalic acid salt, which crystallised after standing for some time with stirring. After standing overnight in the refrigerator it was suction filtered, washed with ether and dried. M.p.: 107°–110° C. The structure was confirmed by NMR spectroscopy. $R_f$ values: 0.53 (ethyl acetate) $R_f$ values: 0.6 (acetonitrile:$H_2O$=9:1)

Preparation of the starting compound:

Part A

Diethyl 4-methoxyphenylmalonate

Ingredients:
150 ml of absolute ethanol
7.5 g (0.33 mol) of sodium
300 ml of diethylcarbonate
62.5 g (0.3 mol) of ethyl 4-methoxyphenylacetate
Method:

Sodium is dissolved in absolute ethanol and evaporated to dryness in vacuo. Whilst cooling with ice water the residue is combined with diethylcarbonate and ethyl 3-chlorophenylacetate, with stirring. Then the ethanol is slowly (2–3 hours) distilled off through a 40 cm column (Raschig rings) under a high vacuum at 40°–70° C. and 200 mM. After cooling, the mixture is acidified with 30 ml of glacial acetic acid and mixed with 150 ml of water. The oil precipitated is washed successively with water and saturated NaCl solution and dried over $MgSO_4$. The residue is distilled in a bulb tube using an oil pump; b.p.: 0.5 mM: 150°–155° C.

Monoethyl 4-methoxyphenylmalonate

Ingredients:
52.2 g (0.196 mol) of diethylester
120 ml of ethanol
120 ml of water
12.3 g (0.22 mol) of KOH in 60 ml of water and 60 ml of ethanol
Method:
An ethanolic solution of diethyl 4-methoxyphenylmalonate is mixed with the aqueous alcoholic KOH solution, with stirring and cooling with ice, and stirred for 75 minutes. Then it is acidified with a saturated citric acid solution and extracted 3 times with methylene chloride. The organic phase is washed successively with water and saturated NaCl solution, dried over $MgSO_4$ and the solvent is distilled off in vacuo. The crystalline residue is recrystallised from methylene chloride/petroleum ether (40–800).

Yield: 34.4 g (73.6% of theory).
The structure was confirmed by NMR spectroscopy.

Monoethyl N-[2,3,4-dimethoxyphenyl)ethyl)-4-
methoxyphenyl-malonate-amide

Ingredients:
34.4 g (0.144 mol) of monoethyl 4-methoxyphenylmalonate
150 ml of anhydrous tetrahydrofuran
23.3 g (0.144 mol) of N,N'-carbonyldiimidazole
26.1 g (0.144 mol) of 2-(3,4-dimethoxyphenyl)ethylamine in 50 ml of anhydrous tetrahydrofuran
Method:

The carbonyldiimidazole is added in batches at 50° C., with stirring, to the solution of the 4-methoxyphenylmalonic acid hemiester in THF. After 30 minutes' stirring at ambient temperature the amine is added whilst cooling with ice and the mixture is stirred for 16 hours at ambient temperature. The reaction mixture is evaporated down and the residue is taken up in $CH_2Cl_2$. It is washed twice with water, then 10% $KHSO_4$ solution, saturated $NaHCO_3$ solution, water and saturated saline solution. After drying over $MgS_4$ the organic phase is evaporated down and the oily residue (7.7 g) is crystallised from ethyl acetate.

4-Methoxy-phenylmalonic acid-N-(2(3,4-
dimethoxyphenyl)ethyl)-amide

Ingredients:
44.16 g (0.11 mol) (4-methoxy-phenylmalonic acid hemiester amide)
300 ml methanol
120 ml (0.12 mol) 1N sodium hydroxide solution
Method:

At 5°–10° C. the sodium hydroxide solution is stirred into the methanolic solution of the hemiester amide for 30 minutes. After 3 hours' stirring at ambient temperature it is evaporated down, diluted with water, then extracted twice with $CH_3Cl$. The aqueous phase is adjusted to pH 1 with concentrated HCl and extracted twice with $CH_3Cl$. After washing with saturated saline solution the organic phase is dried over $MgSO_4$ and evaporated down. The crystalline residue is crystallised from $CH_3Cl$.

Part B 2-(2,3,4-Trimethoxyphenyl)-1-nitro-ethers

Ingredients:
400 g (2.04 mol) of 2,3,4-trimethoxybenzaldehyde
1740 g of glacial acetic acid
172.6 g (2.24 mol) of anhydrous ammonium acetate
656 ml of nitromethane
Method:

The mixture of benzaldehyde, ammonium acetate, nitromethane and glacial acetic acid is stirred for 30 minutes at boiling temperature under nitrogen protection. The mixture is cooled to −5° C. and poured into 5 liters of ice water with stirring. The viscous residue is extracted exhaustively with $CH_2Cl_2$. The organic phase is washed with water, dried over MgSO$_4$ and evaporated down. The brown oily residue (510 g) crystallises on standing. It is dissolved in 470 ml of ethyl acetate and crystallised by the addition of 3.9 liters of cyclohexane.

2-(2,3,4-Trimethoxyphenyl)ethylamine-hydrochloride

Ingredients:
144.5 g (0.60 mol) "Nitrostyrol"
1.9 l of water
232 ml of conc. hydrochloric acid (analytical grade)
88 g PdC (10%)
Method:

The above reaction mixture is hydrogenated at 60° C. under 35 bar for 2.25 hours. Then it is evaporated down in vacuo, the residue is taken up in ethanol and evaporated to dryness. It is then dissolved in ethanol and the reaction product is crystallised by the addition of ether.

2,3,4-Trimethoxybenzylalcohol

Ingredients:
500 g (2.55 mol) 2,3,4-trimethoxybenzaldehyde
5.0 l of methanol 13.0 g of PtO$_2$
Method:

The reduction is carried out at 20° C. under 5 bar and is complete after 30 minutes. After the solvent has been evaporated off the residue (501.5 g) is distilled in a high vacuum (B.p. 116°; 0.5 mbar).

2,3,4-Trimethoxybenzylchloride

Ingredients:
50.0 g (0.25 mol) 2,3,4-trimethoxybenzylalcohol
800 ml of anhydrous methylene chloride
59.4 g (0.5 mol) of thionylchloride
Method:

The solution of the alcohol in anhydrous CH$_2$Cl$_2$ is slowly mixed with SOCl$_2$ with stirring and cooling with ice and common salt. The mixture is stirred for a further 15 minutes in the cold, then for 2 hours at ambient temperature. The solvent and excess thionylchloride are eliminated in vacuo, the residue is taken up in CH$_2$Cl$_2$ and shaken successively with saturated NaHCO$_3$ solution, water and saturated saline solution. After drying over MgSO$_4$ the solvent is removed in vacuo and the residue is distilled in a bulb tube furnace using an oil pump (b.p. 118° C.; 0.1 mbar).

2,3,4-Trimethoxybenzylcyanide

Ingredients:
75.8 g (0.35 mol) 2,3,4-trimethoxybenzylchloride
700 ml of anhydrous acetone
3.45 g (0.023 mol) of NaI
25.7 g (0.53 mol) of dried powdered NaCN
Method:

The reaction mixture consisting of benzyl chloride, NaI and NaCN in anhydrous acetone is stirred for 20 hours at boiling temperature. After cooling it is suction filtered and the solvent is eliminated in vacuo. The residue is dissolved in ethyl acetate, shaken first with water then with saturated saline solution and dried over MgSO$_4$. After removal of the solvent the residue is distilled in a bulb tube furnace at 0.015 mbar (b.p. 135° C.).

2,3,4-Trimethoxyphenylacetic acid

Ingredients:
138.5 g (0.67 mol) 2,3,4-trimethoxybenzylcyanide,
53.5 g (1.34 mol) NaOH dissolved in 215 ml of water
Method:

The mixture of benzyl cyanide and aqueous sodium hydroxide solution is refluxed for 7 hours, then after cooling acidified with 6N H$_2$SO$_4$ and extracted three times with CH$_2$Cl$_2$. The organic phase is washed with water and saturated NaCl solution and dried over MgSO$_4$. After removal of the solvent the residue is dissolved in 200 ml of CH$_2$Cl$_2$ and crystallised by the addition of 1500 ml of cyclohexane.

2,3,4-Trimethoxyphenyl-N-(2-(2,3,4-trimethoxyphenyl)ethyl)-acetamide

Ingredients:
72.4 g (0.32 mol) 2,3,4-trimethoxyphenylacetic acid
400 ml anhydrous tetrahydrofuran
51.8 g (0.32 mol) N,N'-carbonyldiimidazole (CDI)
79.3 g (0.32 mol) 2-(2,3,4-trimethoxyphenyl)ethylamine-hydrochloride
500 ml anhydrous tetrahydrofuran
32.4 ml (0.32 mol) triethylamine
Method:

The phenylacetic acid dissolved in anhydrous THF is converted into the imidazolide with stirring at 5° C. by the batch-wise addition of CDI. After 30 minutes a suspension of amine hydrochloride, triethylamine in anhydrous THF is stirred in at ambient temperature. After 16 hours the mixture is evaporated down in vacuo and the residue is divided between CH$_2$Cl$_2$ and 2N HCl. Then it is washed successively with water, saturated NaHCO$_3$ solution, water and saturated NaCl solution. After drying over MgSO$_4$ the organic phase is evaporated down, the residue is dissolved in 200 ml of ethyl acetate and the product is crystallised by the addition of 700 ml of cyclohexaneo

Di-2-(2,3,4-trimethoxyphenyl)ethylamine-hydrochloride

Ingredients:
113.4 g (0.27 mol) "phenylacetic acid amide"
470 ml anhydrous tetrahydrofuran
270 ml (0.54 mol) BH$_3$.S(CH$_3$)$_2$ in THF (2 mol/l)
Method:

At 65° C. the borane complex mixture is added dropwise to the solution of the acid amide in anhydrous THF under protective N$_2$. After the addition has ended the mixture is stirred for a further 15 minutes at 65° C. Then the reaction mixture is cooled to 5° C. It is carefully acidified with methanolic hydrochloric acid, evaporated down in vacuo (drawn off) and the residue is crystallised from ethanol with the addition of ether.

Part C

4-Methoxy-phenylmalonic acid-N-(2-(3,4-dimethoxyphenyl)ethyl)-N'-(2-(2,3,4-trimethoxyphenyl)ethyl)-di-amide Ingredients:
3.73 g (10 mMol) 4-methoxy-phenylmalonic acid hemiamide
25 ml anhydrous THF
1.62 g (10 mMol) N,N'-carbonyldiimidazole
4.1 g (10 mMol) di-2-(2,3,4-trimethoxyphenyl)ethylaminehydrochloride
40 ml anhydrous THF
1.01 g (10 mMol) triethylamine=1.39 ml
Method:

The carbonyldiimidazole is added in batches to the solution of the monoamide in THF at 5° C. with stirring. The reaction mixture is stirred for 30 minutes at ambient temperature. Then, whilst cooling with ice, it is reacted with a suspension of the amine-hydrochloride in THF and triethylamine. After 16 hours' stirring at ambient temperature it is evaporated down and the residue is dissolved in ethyl acetate. The organic phase is washed successively with water, 5% KHSO₄ solution, saturated NaHCO₃ solution, water and unsaturated NaCl solution. After drying over MgSO₄ the mixture is evaporated down, the residue (7.2 g) is purified on 210 g of silica gel (eluant: ethyl acetate/n-hexane=2:1).

The following Tables contain examples of compounds according to the invention, whilst Tables 10 to 20 list new compounds.

TABLE 1

Structural type:

| No. | X | Structure | Salt form |
|---|---|---|---|
| 1. | OCH₃ | II | — |
| 2. | OC₂H₅ | II | — |
| 3. | NHCH₃ | I | Cl |
| 4. | NHC₂H₅ | I | — |
| 5. | NH—(CH₂)₂—CH₃ | I | Cl |
| 6. | NH—(CH₂)₃—CH₃ | I | Cl |
| 7. | NH—(CH₂)₄—CH₃ | I | Cl |
| 8. | NH—CH(CH₃)₂ | I | Cl |
| 9. | NH—CH₂—CH(CH₃)₂ | I | Cl |
| 10. | NH—(CH₂)₂—CH(CH₃)₂ | I | Cl |
| 11. | NH—C(CH₃)₃ | I | Cl |
| 12. | NH—CH(CH₃)—C₂H₅ | I | Cl |
| 13. | NH—CH₂—CH=CH₂ | I | Cl |
| 14. | NH—CH₂—C≡CH | I | Cl |
| 15. | NH—(CH₂)₂—OH | II | Cl |
| 16. | NH—CH₂—CH(OH)—CH₃ | I | Cl |
| 17. | NH—(CH₂)₂—OCH₃ | II | Cl |
| 18. | NH—(CH₂)₃—OCH₃ | II | Cl |
| 19. | NH—(CH₂)₂—N(CH₃)₂ | I | Cl₂ |
| 20. | NH—(CH₂)₃—N(CH₃)₂ | II | Cl₂ |
| 21. | NH—(CH₂)₂—N⟨O⟩ (morpholine) | II | — |
| 22. | NH—(CH₂)₂—phenyl | I | Cl |
| 23. | NH—(CH₂)₂—(benzodioxole) | I | — |

TABLE 1-continued

Structural type:

| No. | X | Structure | Salt form |
|---|---|---|---|
| 24. | NH—(CH₂)₂—(2,4-dimethoxyphenyl) | I | — |
| 25. | NH—(CH₂)₂—(4-methoxyphenyl) | I | — |
| 26. | NH—(CH₂)₂—(3,4-dimethoxyphenyl) | II | — |
| 27. | NH—(CH₂)₂—(2-methoxyphenyl) | II | Cl |
| 28. | NH—(CH₂)₂—(2-methoxy-4-hydroxyphenyl) | I | — |
| 29. | NH—(CH₂)₂—(pyridyl) | I | — |
| 30. | NH—(CH₂)₂—(indolyl) | II | — |
| 31. | NH—N⟨O⟩ (morpholine) | I | — |
| 32. | NH—CH₂—(furyl) | II | — |
| 33. | NH—(pyridyl) | I | Cl |
| 34. | NH—(cyclopropyl) | I | Cl |

TABLE 1-continued

Structural type:

[Structure: 6,7-dimethoxy-3,4-dihydroisoquinoline with =C(Ph)-C(=O)-X substituent at position 1]

| No. | X | Structure | Salt form |
|---|---|---|---|
| 35. | NH-cyclohexyl | II | — |
| 36. | N(CH₃)₂ | I | Cl |
| 37. | N(C₂H₅)₂ | I | Cl |
| 38. | N(CH₂-CH₂-(3,4,5-trimethoxyphenyl))₂ | I | Cl |
| 38a. | N(CH₂-CH₂-(2,3,4-trimethoxyphenyl))₂ | I | Cl |
| 39. | morpholino (N-O ring) | I | Cl |
| 40. | thiomorpholino (N-S ring) | I | — |
| 41. | pyrrolidino | II | — |
| 42. | 4-benzylpiperazino | II | Cl₂ |
| 43. | 4-methylpiperazino | I | — |
| 44. | 4-(2-methoxyphenyl)piperazino | I | Cl |

TABLE 2

Structural type:

[Structure: 6,7-methylenedioxy-3,4-dihydroisoquinoline with =C(Ph)-C(=O)-X substituent at position 1]

| No. | X | Structure | Salt form |
|---|---|---|---|
| 45. | OC₂H₅ | II | — |
| 46. | NH-(CH₂)₂-(3,4-methylenedioxyphenyl) | II | Cl |
| 47. | NH-(CH₂)₂-(3-indolyl) | II | — |
| 48. | NH-(CH₂)₂-morpholino | II | — |
| 49. | morpholino | II | — |
| 50. | pyrrolidino | I | — |

TABLE 3

Structural type:

[Structure: 6-methoxy-7-hydroxy-3,4-dihydroisoquinoline with =C(Ph)-C(=O)-X substituent at position 1]

| No. | X | Structure | Salt form |
|---|---|---|---|
| 51. | OC₂H₅ | I, II | — |
| 52. | NH-(CH₂)₃-CH₃ | I | — |
| 53. | NH-(CH₂)₄-CH₃ | I | — |
| 54. | NH-CH(CH₃)₂ | I | Cl |
| 55. | NH-CH₂-CH(CH₃)₂ | I | — |
| 56. | NH-CH₂-CH=CH₂ | I | — |
| 57. | NH-(CH₂)₂-phenyl | I | Cl |

TABLE 3-continued

Structural type:

(isoquinoline core with H3CO, HO substituents, Ph, C(=O)–X)

| No. | X | Structure | Salt form |
|---|---|---|---|
| 58. | NH—(CH₂)₂—(3,4-dimethoxyphenyl) [OCH₃, OCH₃] | I | Cl |
| 59. | NH—(CH₂)₂—(3-methoxy-4-hydroxyphenyl) [OCH₃, OH] | I | — |
| 60. | NH—(CH₂)₂—(2-pyridyl) | I | — |
| 61. | NH—(CH₂)₂—N(morpholino) | I | — |
| 62. | NH—(3-chlorophenyl) | I | — |
| 63. | NH—(2-methyl-3-chlorophenyl) | I | Cl |
| 64. | NH—(2-pyridyl) | I | — |
| 65. | NH—(3-pyridyl) | I | Cl |
| 66. | piperazinyl—(2-methoxyphenyl) | I | Cl |
| 67. | morpholino | I | Cl |

TABLE 3-continued

Structural type:

(isoquinoline core with H3CO, HO substituents, Ph, C(=O)–X)

| No. | X | Structure | Salt form |
|---|---|---|---|
| 68. | N(CH₂—CH₂—CN)(CH₂—Ph) | I | Cl |

TABLE 4

Structural type:

(isoquinoline core with HO, H3CO substituents, Ph, C(=O)–X)

| No. | X | Structure | Salt form |
|---|---|---|---|
| 69. | N(C₂H₅)₂ | I | — |

TABLE 5

Structural type:

(isoquinoline core with H3CO substituent, Ph, C(=O)–X)

| No. | X | Structure | Salt form |
|---|---|---|---|
| 70. | NHCH₅ | I | |
| 71. | NHC₂H₅ | I | |
| 72. | NH—CH₂—(phenyl) | I | |
| 73. | NH(CH₂)₂—(3-methoxyphenyl) | I | |
| 74. | N(CH₃)C₂H₅ | I | |

TABLE 6

Structural type:

[Structure: 2-(3,4,5-trimethoxyphenyl)ethyl-N=C(Ph)(COX) dihydroisoquinoline-type]

| No. | X | Structure |
|---|---|---|
| 75. | NH—CH₂—C₆H₅ | I |
| 76. | NH—(CH₂)₂—(2,3,4-trimethoxyphenyl) | I |
| 77. | N(CH₃)C₂H₅ | I |
| 78. | NH—(3-pyridyl) | II |
| 79. | 4-methylpiperazin-1-yl | I |

TABLE 7

Structural type:

[β-carboline-type with Ph-C(=O)X substituent]

| No. | X | Structure | Salt form |
|---|---|---|---|
| 82. | OC₂H₅ | I | — |
|     |       | II | — |
| 83. | NH—(CH₂)₂—(2,3-dimethoxyphenyl) | II | — |

TABLE 7-continued

Structural type:

[β-carboline-type with Ph-C(=O)X substituent]

| No. | X | Structure | Salt form |
|---|---|---|---|
| 84. | NH—(CH₂)₂—(2,3-methylenedioxyphenyl, ethylenedioxy) | II | — |
| 85. | NH—(CH₂)₂—(indol-3-yl) | I | — |
|     |   | II | — |
| 86. | morpholin-4-yl | I | — |
| 87. | NH—CH₂—CH(CH₃)₂ | II | — |
| 88. | NH—(CH₂)₃—N(CH₃)₂ | II | — |
| 89. | NH—(CH₂)₂—morpholin-4-yl | II | — |

TABLE 8

Structural type:

[thieno-pyridine-type with Ph-C(=O)X substituent]

| No. | X | Structure | Salt form |
|---|---|---|---|
| 90. | OC₂H₅ |   |   |
| 91. | NH—(CH₂)₂—(2-thienyl) | II | — |

TABLE 9

Structural type I: 6,7-dimethoxy-3,4-dihydroisoquinoline with -CH(C₆H₅)-C(=O)-X substituent at position 1

Structural type II (II' or II"): 6,7-dimethoxy-1,2,3,4-tetrahydroisoquinoline with exocyclic =C(C₆H₅)(COX) or =C(COX)(C₆H₅) double bond at position 1

| Compound | X | Structural type | Mp [°C.] |
|---|---|---|---|
| A | –N(CH₂CH₂-[2,3,4-trimethoxyphenyl])₂ · HCl | I | 56–64 |
| B | –NH–CH₂CH₂-[2,3,4-trimethoxyphenyl] · HCl | I | 176–184 |
| Compound (Salt form) | | | |
| C | –NH–CH₂–CH(C₆H₅)₂ | I | 166–168 |
| D | –NH–CH₂–CH₂-(2-thienyl) | II | 102–104 |
| E (Cl) | –NH–CH₂–CH₂-(3-trifluoromethylphenyl) | I | 187 |

TABLE 9-continued
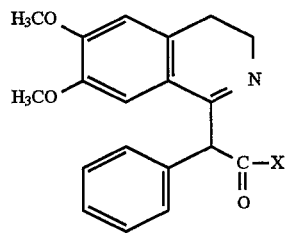
Structural type I
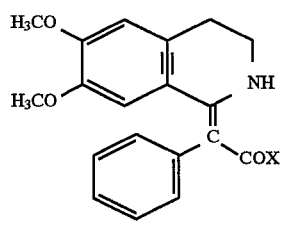 or 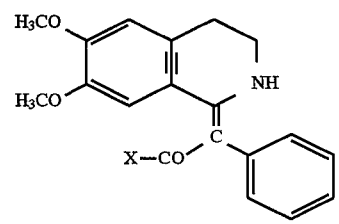
II'  II''
Structural type II
| X | | Structural type | Mp [°C.] |
|---|---|---|---|
| F (—) | -NH-CH₂-(2-F, 6-OCH₃-phenyl) | I | 94–96 |
| G (Cl) | -NH-CH₂-CH₂-(2,3-di-OCH₃-phenyl) | II | 139–142 |
| H (—) | -NH-CH(CH₃)-CH₂-O-phenyl | II | 133–135 |
| J (—) | -NH-CH₂-(2-OCH₃-phenyl) | II | 143–145 |
| K (—) | -NH-CH₂-CH₂-(2-OC₂H₅-phenyl) | II | 96–98 |
| L (—) | -NH-CH₂-CH₂-(2,6-di-OCH₃-phenyl) | II | 118–120 |

TABLE 9-continued
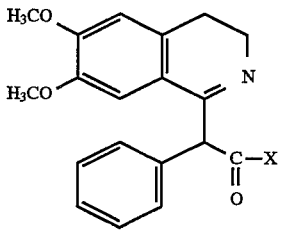
Structural type I
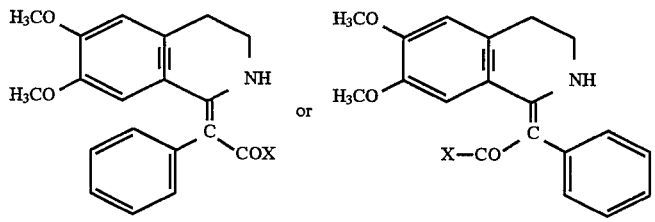
Structural type II
| X | | Structural type | Mp [°C.] |
|---|---|---|---|
| M (—) | 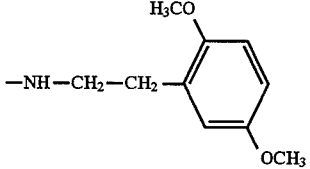 | II | 112–114 |
| N (Cl) | 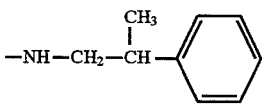 | I | 95–99 |
| O (—) | 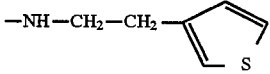 | I | 114–116 |
| P (—) | 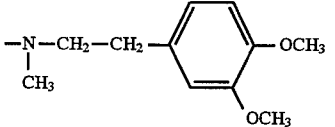 | I | 66–73 |
| Q (Cl) | 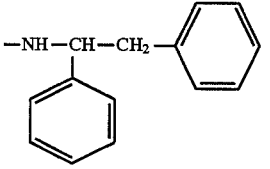 | II | 205–209 |

TABLE 10

Structural type:

[Structure: 6,7-dimethoxy-3,4-dihydroisoquinoline with =C(Ph)-C(=O)-X substituent at position 1]

| No. | X | Structure | Salt form | Mp [°C.] |
|---|---|---|---|---|
| 101 | —NH—CH₂—CH₂—CH(Ph)₂ | I | Oxalate | 138–140 |
| 102 | —NH—CH₂—CH₂—(2-methylphenyl) | I | Oxalate | 153–155 |
| 103 | —N(piperidinyl) | I | Oxalate | 117–123 |
| 104 | —NH—CH₂—CH₂—(3,5-dimethoxyphenyl) | I | Oxalate | 154–155 |
| 105 | —NH—CH₂—CH₂—(3-methoxyphenyl) | I | Oxalate | 127–129 |
| 106 | —NH—CH₂—(2,5-dimethylphenyl) | I | Oxalate | 132–135 |
| 107 | —NH—CH₂—CH(Ph)—CH₃ | I | Oxalate | 145–147 |
| 108 | —NH—(CH₂)₃—(2,3,4-trimethoxyphenyl) | I | Base | 118–120 |
| 109 | —NH—CH₂—CH₂—(2,6-dimethyl-3-methoxyphenyl) | II | Base | 118–120 |

TABLE 10-continued
Structural type:
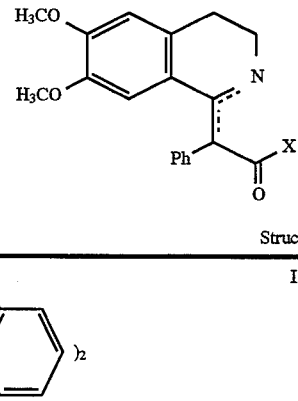
| No. | X | Structure | Salt form | Mp [°C.] |
|---|---|---|---|---|
| 110 | 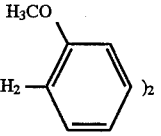 | I | Oxalate | 153–156 |
| 111 | —N[(CH$_2$)$_5$CH$_3$]$_2$ | I | Oxalate | 81–84 |
| 112 | —N(CH$_2$CH$_2$CH$_3$)$_2$ | I | Oxalate | 57–59 |
| 113 | —N[(CH$_2$)$_4$CH$_3$]$_2$ | I | Oxalate | — |
| 114 |  | I | Oxalate | 125–126 |
| 115 |  | I | Base | 103–105 |
| 116 | —N[(CH$_2$)$_3$CH$_3$]$_2$ | I | Oxalate | 119–121 |
| 117 | —N[CH$_2$CH(CH$_3$)$_2$]$_2$ | I | Oxalate | 130–131 |
| 118 | 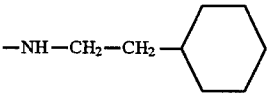 | I | Oxalate | 176–178 |
| 119 | 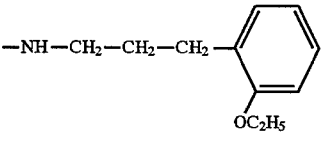 | I | Oxalate | 160–162 (Decomp) |
| 120 |  | I | Oxalate | 170–172 |
| 121 | 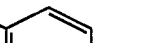 | I | Oxalate | 158–160 (Decomp) |
| 122 | 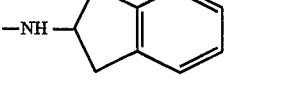 | I | Oxalate | 166–168 |
| 123 | —NH—(CH$_2$)$_9$—CH$_3$ | I | Oxalate | 99–101 |
| 124 | 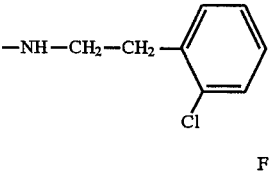 | I | Oxalate | 127–143 |

TABLE 10-continued

Structural type:

[Structure: 6,7-dimethoxy-3,4-dihydroisoquinoline with =C(Ph)–C(=O)–X substituent at position 1]

| No. | X | Structure | Salt form | Mp [°C.] |
|---|---|---|---|---|
| 125 | —N(CH₂—CH₂—C₆H₄-F(o))₂ | I | Oxalate | 144–149 |
| 126 | —N—(CH₂—C₆H₅)₂ | I | Oxalate | 137–139 |
| 127 | —NH—CH₂CH₂—(2,5-dimethoxyphenyl) | I | HCl | 185–187 |
| 128 | —N(CH₂CN)₂ | I | Base | |
| 129 | —NH—cyclohexyl | II | Base | |
| 130 | —NH—CH₂—cyclohexyl | II | HCl | |
| 131 | —NH—C₆H₅ | II | HCl | |
| 132 | —NH—CH₂-Adam(1) | II | HCl | |
| 133 | —NH—CH₂—CH₂—(2-methoxy-4-azidophenyl) | I | Oxalate | |
| 134 | —N((CH₂)₅COOC₂H₅)((CH₂)₁₀—COOC₂H₅) | I | Base | |
| 135 | —NH—CH₂—CH₂—(2-methoxy-4-azido-5-iodophenyl) | I | HCl | |

TABLE 10-continued

Structural type:

[Structure: 6,7-dimethoxy-3,4-dihydroisoquinoline with =C(Ph)-C(=O)-X substituent at position 1]

| No. | X | Structure | Salt form | Mp [°C.] |
|-----|---|-----------|-----------|----------|
| 136 | —N(CH₂—CH₂—C₆H₃(OCH₃)₂)(CH₂—CH(CH₃)₂) [3,4-dimethoxyphenethyl / isobutyl] | I | HCl | |
| 137 | —N(piperazine)—CH₂—CH₂—O—C₆H₄(OCH₃) [3-methoxyphenoxyethyl piperazine] | I | (Oxalate)₂ | |
| 138 | —NH—CH(CH₃)—CH₂—O—C₆H₃(CH₃)₂ [2,6-dimethylphenoxy] | I | HCl | |
| 139 | —N(CH₃)—CH(CH₃)—CH₂—O—C₆H₃Cl₂ [2,6-dichlorophenoxy] | I | HCl | |
| 140 | —NH—CH₂—CH₂—O-(1-naphthyl) | I | Base | |
| 141 | —O—CH₂—C(CH₃)₃ | II | Base | |
| 142 | —O—CH₂—C₆H₅ | II | Base | |
| 143 | —O—CH₂CH₂-Adam(1) | II | HCl | |
| 144 | —O—CH₂—CH₂—C(CH₃)₃ | II | HCl | |
| 145 | —O—CH₂-Adam(1) | II | Base | |
| 146 | —O—CH₂—CH₂-cyclohexyl | II | HCl | |
| 147 | —O—CH₂-cyclohexyl | II | HCl | |

TABLE 10-continued
Structural type:
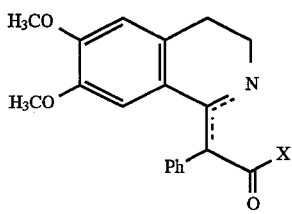
| No. | X | Structure | Salt form | Mp [°C.] |
|---|---|---|---|---|
| 148 | NH—CH₂—(2-F-C₆H₄) | I | Oxalate | 118–120 |
| 149 | NH—CH₂—(2,3-(OCH₃)₂-C₆H₃) | I | HCl | 195–197 |
| 150 | NH—CH₂—(2-CF₃-C₆H₄) | I | HCl | 140–143 |
| 151 | NH—CH₂—(2-CH₃-C₆H₄) | I | HCl | 193–195 |
| 152 | NH—(3,4,5-(OCH₃)₃-C₆H₂) | I | HCl | 155–158 |
| 153 | NH—CH₂—(2-OC₂H₅-C₆H₄) | I | HCl | 168–170 |
| 154 | NH—CH₂—(2,3-methylenedioxy-C₆H₃) | I | HCl | 172–174 |
Adam = Adamantyl

TABLE 11
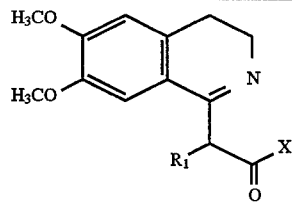
| R₁ | X | Salt form | |
|---|---|---|---|
| 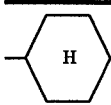 | 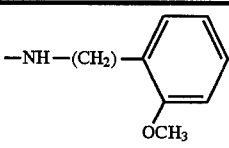 | HCl | Mp. 116–127° C. |
| 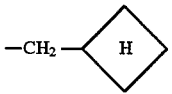 | 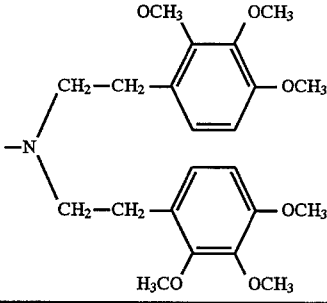 | BS | Rf: 0.39 (ethyl acetate) |
TABLE 12
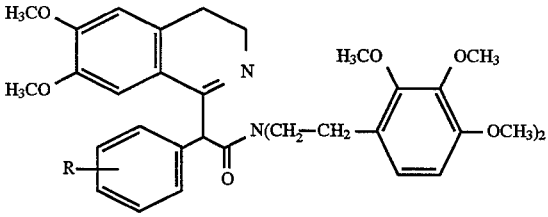
| No. | R | Structure | Salt form | Mp [°C.] |
|---|---|---|---|---|
| 1 | 4-CH₃ | I | Oxalate | |
| 2 | 4-F | I | Oxalate | |
| 3 | 3-Cl | I | Oxalate | |
| 4 | 4-Br | I | Oxalate | |
| 5 | 2-OCH₃ | I | Oxalate | |
| 6 | 3-OCH₃ | I | Oxalate | |
| 7 | 4-OCH₃ | I | Oxalate | |
| 8 | 3,4-di-OCH₃ | I | Oxalate | |
| 9 | 3,4,5-tri-OCH₃ | I | Oxalate | |
| 10 | 4-N₃ | I | Oxalate | |
| 11 | 3-I,4-N₃ | I | Oxalate | |
| 12 | 2-CH₃ | I | Oxalate | |
| 13 | 2-Br | I | Base | |
| 14 | 2,4-di-Cl | I | Oxalate | |
| 15 | 3-F | I | Oxalate | |
| 16 | 2-Cl | I | Base | |

TABLE 13
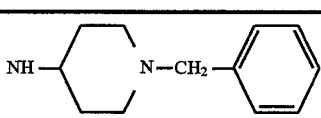
| No. | NR³R⁴ | Salt form | Structure | Mp (°C.) | % Inhib. |
|---|---|---|---|---|---|
| | 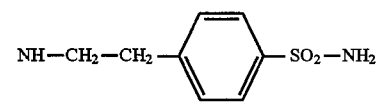 | 1.5 Fu | I | 177–178 | 40.44 |
| | " | BS | II | 158–159 | 0.0 |
| | 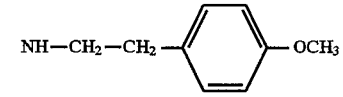 | BS | II | 165–167 | 50.64 |
| | 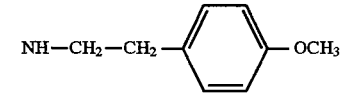 | MS | I | 132–133 | 67.73 |
| | 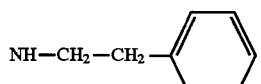 | BS | II | 84–55 | 65.50 |
| | 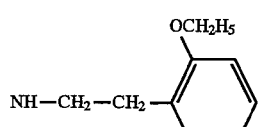 | MS | I | 151–153 | 80.89 |
| | " | BS | II | 110–111 | 39.47 |
| | 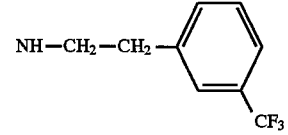 | MS | I | 118–122 | 24.03 |
| | 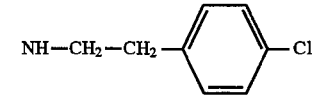 | MS | I | 150–154 | 43.49 |
| | 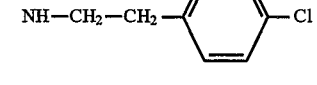 | Cl | I | 144–147 | 15.26 |
| | 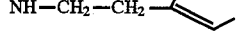 | BS | II | 131–133 | 26.54 |
| | 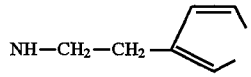 | Cl | I | 114–115 | 0.0 |
| | 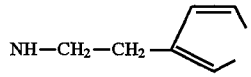 | BS | II | 144–147 | 67.75 |

TABLE 14

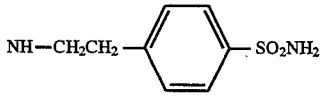

| No. | NR³R⁴ | Salt form | Structure | Mp (°C.) | % Inhib. |
|-----|-------|-----------|-----------|----------|----------|
| | NH—CH₂CH₂—C₆H₄—SO₂NH₂ | Cl | I | amorphous[x] | 79.17 |
| | NHCH₂CH₂CH₂—C₆H₅ | Cl | I | amorphous[x] | 73.55 |
| | NH—CH₂—CH₂—(N-methylpyrrolidin-2-yl) | Cl | I | amorphous[x] | 60.82 |
| | NH—CH(CH₃)—CH₂—CH₂—C₆H₅ | Cl | I + II | amorphous[x] | 82.76 |
| | NH—CH₂—(3,4-dimethoxyphenyl) | Cl | I | amorphous[x] | 50.90 |
| | NH—CH₂—(2,4-dimethoxyphenyl) | Ox | I | amorphous[x] | 56.20 |
| | N(CH₂CH₂—(2-chlorophenyl))₂ | Ox | I | 142–144 | |
| | N((CH₂)₃—C₆H₅)₂ | BS | I | 105–106 | 22.39 |
| | 4-benzylpiperazin-1-yl | Cl₂ | I | 208–210 | |
| | NH—CH₂CH₂—(4-methylphenyl) | MS | I | amorphous[x] | 79.60 |

TABLE 14-continued

Structure I: 6,7-dimethoxy-3,4-dihydroisoquinoline with CH connected to phenyl and C(=O)NR³R⁴

Structure II: enamine tautomer with NH

| No. | NR³R⁴ | Salt form | Structure | Mp (°C.) | % Inhib. |
|---|---|---|---|---|---|
| | NH—CH₂—CH₂—(2-OCH₂Ph, 6-Cl-phenyl) | Cl | I | amorphous[x)] | 36.71 |
| | NH—CH₂—cyclohexyl | Cl | I | amorphous[x)] | 30.87 |

[x)] The structure of the substance is characterised by NMR spectroscopy

TABLE 15

Structure I: 6,7-dimethoxy-3,4-dihydroisoquinoline with CH connected to cyclohexyl and C(=O)NR³R⁴

| No. | NR³R⁴ | Salt form | Structure | Mp (°C.) | % Inhib. |
|---|---|---|---|---|---|
| | NH—CH₂CH₂—phenyl | Cl | I | 134–136 | |
| | NH—CH₂—CH₂—(4-Cl-phenyl) | Cl | I | 166–168 | |
| | NH—CH₂—cyclohexyl | Cl | I | 142–144 | |
| | NH—(CH₂)₃—(4-C(CH₃)₃-phenyl) | BS | I | 119 | 84.43 |

TABLE 16

[Structure: 3,4-dihydroisoquinoline with R^a, R^b substituents on benzene ring; position 1 bears CH(phenyl)-C(=O)-NR^3R^4]

| No. | Salt form | R^a | R^b | NR^3R^4 | Mp. | % H | IC$_{50}$ |
|---|---|---|---|---|---|---|---|
| | MS | HO— | CH$_3$O— | —N—(CH$_2$—CH$_2$—C$_6$H$_2$(OCH$_3$)$_3$ [2,3,4-trimethoxyphenethyl])$_2$ | | 87 | 3.47 × 10$^{-6}$ |
| | MS | CH$_3$O— | HO— | " | | 0 | — |
| | MS | CH$_3$O— | CH$_3$O— | —N(CH$_2$CH$_2$-2,3,4-trimethoxyphenyl)(CH$_2$CH$_2$-2,3,4-trimethoxyphenyl) | | | |
| | OX | CH$_3$O— | H— | —NH—CH$_2$—CH$_2$—C$_6$H$_4$(CF$_3$) [3-CF$_3$] | 60–70 | 30.41 | |
| | MS | C$_6$H$_5$—CH$_2$—O— | H— | " | 182–185 | 14.65 | |
| | OX | HO— | H— | " | 120–130 | | |
| | OX | CH$_3$O— | CH$_3$— | " | 143 | 10.47 | |
| | OX | C$_6$H$_5$—CH$_2$O— | CH$_3$— | " | 156–157 | 49.03 | |
| | OX | HO— | CH$_3$— | " | 80–95 | | |
| | OX | CH$_3$— | Cl— | " | 143–145 | 44.65 | |
| | OX | C$_6$H$_5$—CH$_2$O— | Cl— | " | 130–132 | 32.90 | |
| | OX | HO— | Cl— | " | 182–183 | | |
| | MS | C$_6$H$_5$—CH$_2$—O— | CH$_3$— | " | | 31.8 | |

TABLE 16-continued

| No. | Salt form | $R^a$ | $R^b$ | $NR^3R^4$ | Mp. | % H | $IC_{50}$ |
|---|---|---|---|---|---|---|---|
| | MS | $CH_3O-$ | $C_6H_5-CH_2O-$ | " | | 22.9 | |
| | OX | $CH_3O-$ | $CH_3-$ | $-N(CH_2-C_6H_5)_2$ | 145–151 | 58.3 | |
| | OX | $CH_3O-$ | $H-$ | " | 115–125 | | |
| | OX | $CH_3O-$ | $Cl-$ | " | 131–135 | | |
| | OX | $C_6H_5-CH_2-O-$ | $Cl-$ | " | 135–142 | | |
| | OX | $C_6H_5-CH_2-O-$ | $CH_3-$ | " | 162–164 | | |
| | OX | $C_6H_5-CH_2-O-$ | $H-$ | " | 145–147 | | |
| | OX | $HO-$ | $Cl-$ | " | 187–190 | | |
| | OX | $HO-$ | $CH_3-$ | " | 193–200 | | |
| | OX | $HO-$ | $H-$ | " | 154–157 | | |

TABLE 17

| No. | $NR^3R^4$ | Salt form | Mp (°C.) | % Hem. | $IC_{50}$ |
|---|---|---|---|---|---|
| | $-HN-CH_2-CH_2-$(2-$CH_3O$, 4-$N_3$)-$C_6H_3$ | OX | amorphous* | 68.2 | |

TABLE 17-continued

[Structure: 6,7-dimethoxy-3,4-dihydroisoquinoline with CH(phenyl)-C(=O)-NR³R⁴ substituent at position 1]

| No. | NR³R⁴ | Salt form | Mp (°C.) | % Hem. | IC₅₀ |
|-----|-------|-----------|----------|--------|------|
| | —HN—CH₂—CH₂—(phenyl with CH₃O, N₃, I) | Cl | amorphous* | 36.95 | |
| | —HN—CH₂—CH₂—(phenyl with CH₃O) | Cl | | 69.7 | |
| | —HN—(phenyl) | Cl | amorphous* | | |
| | —HN—(cyclohexyl) | BS | amorphous* | | |
| | —HN—CH₂—(cyclohexyl) | Cl | amorphous* | | |
| | —HN—CH₂-1-Adam. | Cl | amorphous* | 65.1 | |
| | —N(CH₂—CN)(CH₂—CN) | BS | amorphous* | | |
| | —N(CH₂—CH₂—(3,4-dimethoxyphenyl))(CH₂—CH(CH₃)CH₃) | Cl | amorphous* | 12.82 | |
| | —HN—CH₂—CH₂—O—(1-naphthyl) | BS | amorphous* | 59 | |
| | —HN—CH(CH₃)—CH₂—O—(2,6-dimethylphenyl) | Cl | amorphous* | 72.18 | |

TABLE 17-continued

[Structure: 6,7-dimethoxy-3,4-dihydroisoquinoline with CH(phenyl)-C(=O)-NR³R⁴ substituent at position 1]

| No. | NR³R⁴ | Salt form | Mp (°C.) | % Hem. | IC$_{50}$ |
|---|---|---|---|---|---|
| | —N(CH(CH₃)—CH₂—O—(2,6-dichlorophenyl)) | Cl | amorphous* | | |
| | —N(piperazinyl-N—CH₂—CH₂—O—(3-methoxyphenyl)) | OX-2 | amorphous* | 41.06 | |
| | —N(piperazinyl) attached via CH—N to (4,5-dimethoxyphenyl)-CH(NH₂) | BS | amorphous* | 7.77 | |
| | HN—CH₂—CH₂—O—(3-methoxyphenyl) | BS | amorphous* | 45.26 | |
| | —N(6-methoxy-1,2,3,4-tetrahydroisoquinolin-2-yl) | OX | amorphous* | 33.06 | |
| | —NH—C(CH₃)₃ | Cl | 199–201 | 81.60 | |
| | —NH—CH₂—C(CH₃)₃ | Cl | amorphous* | 52.51 | |
| | —NH—CH₂—CH₂—C(CH₃)₃ | Cl | amorphous* | 80.97 | 7.57 × 10⁻⁶ |

*The structure of the substance is characterised by NMR spectroscopy

TABLE 18

Structure:
4,5-dimethoxy-3,4-dihydroisoquinoline with C(R¹)H-CO-N(CH₂CH₂-[2,3,4-trimethoxyphenyl])₂ substituent at position 1

| No. | R¹ | Salt form | Mp. | % Hem. | IC₅₀ |
|---|---|---|---|---|---|
| | 2-methoxyphenyl | OX | amorphous* | 41.8 | |
| | 3-methoxyphenyl | OX | amorphous* | 24.3 | |
| | 4-methoxyphenyl | OX | amorphous* | 73.7 | |
| | 3,4-dimethoxyphenyl | OX | amorphous* | 53.1 | |
| | 3,4,5-trimethoxyphenyl | OX | amorphous* | | |
| | 2,3-dimethylphenyl | OX | amorphous* | 68.22 | |
| | 4-methylphenyl | OX | amorphous* | | |
| | 2-bromophenyl | BS | amorphous* | | |
| | 4-bromophenyl | OX | amorphous* | | |

TABLE 18-continued

| No. | R¹ | Salt form | Mp. | % Hem. | IC₅₀ |
|---|---|---|---|---|---|
| | 2-chlorophenyl | BS | amorphous* | | |
| | 3-chlorophenyl | OX | amorphous* | | |
| | 2,3-dichlorophenyl | OX | amorphous* | 30.79 | |
| | 2-fluorophenyl | OX | amorphous* | | |
| | 3-fluorophenyl | OX | amorphous* | | |
| | 4-fluorophenyl | OX | amorphous* | 54.30 | |
| | 4-azidophenyl | OX | amorphous* | 61.3 | |
| | 3-azido-4-iodophenyl | Cl | amorphous* | 5.81 | |
| | cyclohexylmethyl | BS | amorphous* | | |
| | cyclobutylmethyl | | amorphous* | 56.0 | |

TABLE 18-continued

[Structure: 6,7-dimethoxy-3,4-dihydroisoquinoline with CH(R¹)–CO–N(CH₂CH₂-(2,3-dimethoxy-4-methoxyphenyl))₂ substituent at position 1]

| No. | R¹ | Salt form | Mp. | % Hem. | IC₅₀ |
|-----|----|-----------|-----|--------|------|
| | 3,4,5-trimethoxyphenyl (CH₃O, CH₃O, OCH₃) | OX | amorphous* | | |
| | 2-fluorophenyl | OX | amorphous* | | |

*: The structure of the substance is characterised by NMR spectroscopy

TABLE 19

[Structure: 6,7-dimethoxy-3,4-dihydroisoquinoline with CH(4-N₃-phenyl)–C(O)–NH–CH₂CH₂-(2-methoxyphenyl) substituent]

OX    amorphous*
% Hem: 50.58

*: The structure of the substance is characterised by NMR spectroscopy

TABLE 20

[Structure: 3,4-dihydroisoquinoline with Rᵃ, Rᵇ substituents on the aromatic ring and CH(phenyl)–C(O)–NR³R⁴ group]

| No. | Rᵃ | Rᵇ | NR³R⁴ | Salt form | Mp. | % H | IC₅₀ |
|-----|----|----|-------|-----------|-----|-----|------|
| | HO— | CH₃O— | N(—CH₂CH₂-(2,3-dimethoxy-4-methoxyphenyl))₂ | MS | 163–169 | 86.70 | 3.47×10⁻⁶ |
| | Ph-CH₂—O— | CH₃O— | " | MS | amorph* | 31.78 | |
| | Ph-CH₂O— | CH₃O— | NH—CH₂CH₂—C(CH₃)₃ | OX | amorph* | 61.85 | |

TABLE 20-continued

[Structure: isoquinoline-type compound with $R^a$, $R^b$ substituents on benzene ring, a CH-phenyl group, and C(=O)-NR³R⁴ group]

| No. | $R^a$ | $R^b$ | $NR^3R^4$ | Salt form | Mp. | % H | $IC_{50}$ |
|-----|-------|-------|-----------|-----------|-----|-----|-----------|
|     | Ph-CH₂—O— | Cl— | NH—CH₂CH₂—(3-CF₃-phenyl) | OX | 130–132 | 32.9 | |
|     | CH₂O— | Cl— | " | OX | 143–145 | 44.65 | |
|     | Ph-CH₂—O— | CH₃— | " | OX | 156–157 | 49.03 | |

*The structure of the substance is characterised by NMR spectroscopy

The present invention further relates to the use of the above-mentioned compounds for the production of agents for treating chronic inflammatory processes, ulcerative colitis and Crohn's disease and for producing agents having an antiproliferative effect. The activity of the compounds can be explained by their inhibition of the unselective cation channels (UCC).

The pathophysiology of chronic bronchial asthma is based on inflammatory processes which are mediated by the activation of inflammatory cells. (BARNES, 1987; SEIFERT and SCHULTZ, 1991).

The receptor-regulated activation of inflammatory cells (e.g. neutrophilic granulocytes and mast cells or the permanent cell lines HL-60 cells or sensitised RBL cells, i.e. those charged with gammaglobulin E) is inhibited, irrespective of the nature of the stimulating agonists (e.g. endothelin, PAF, leukotrienes, chemotactical peptide fMLP or antigen against sensitised mast cells) by blockers of unselective cation channels (UCC) (RINK, 1990). Through these channels extracellular calcium, which is responsible for the persistence of receptor-mediated cell activations, enters the cells (PUTNEY, 1990). If this supply of calcium is interrupted this results in a blockade of the activation of inflammatory cells.

Conventional calcium antagonists of the dihydropyridine or phenylalkylamine type do not inhibit either UCCs or inflammatory processes (WELLS et al., 1986).

As a measurement of the cell activation or as a measurement of the inhibition thereof by UCC blockers, the kinetics of the cytoplasmic calcium ion concentration in fura-2-charged cells is quantified fluorometrically using the method described by GRYNKIEWICZ et al. (1985). This procedure has proved a reliable screening method, within the scope of the invention, for detecting UCC blockers.

So-called functional THAPSIGARGIN inhibition has proved suitable for the specific characterisation of blockers of the unselective cation channels. THAPSIGARGIN is a tumour promoter described by THASTRUP et al. (Proc. Natl. Acad. Sci. (USA), 87, 2466–2470, 1990) which selectively and irreversibly inhibits the $Ca^{2+}$-ATPase of intracellular IP₃-sensitive $Ca^{2+}$-storeso Consequently the $Ca^{2+}$-stores are rapidly depleted. As described by J. PUTNEY (Calcium, 11, 611–624, 1990) the depletion of these stores constitutes the physiological stimulation for opening up unselective cation channels in the cell membrane. The result of this is a massive influx of $Na^+$ and $Ca^{2+}$ into the cell. Because of these properties, Thapsigargin is suitable as an indirect stimulator for agohist- and IP₃-independent opening up of the unselective cation channels.

Within the scope of the present invention the Thapsigargin stimulation of unselective cation channels has been carried out successfully on HL-60 cells (human leukaemia cells), on hippocampal and cortical neurone cells and on RBL-cells (rat basophilic lymphoma cells) and in this way the existence of these channels in particular cell lines was demonstrated.

The cytoplasmic $Ca^{2+}$ concentration ($[Ca^{2+}]_i$) plays an important part in the cell proliferation and in tumour growth (for a summary see L. R. ZACHARSKI, Journal of Medicine 19: 145–177, 1988). In particular, the $Ca^{2+}$-influx into the cell stimulated by receptor activation with consecutive inositoltriphosphate-(IP₃-)-mediation would appear to be of crucial importance for oncogenic cell proliferation (U. KIKKAWA and Y. NISHIZUKA, Ann. REV. CELL. BIOL. 2: 149–178, 1986). This mechanism also plays a part in the formation of metastases and in "Multi-Drug Resistance". (For a summary see the abovementioned mentioned publication by L. R. ZACHARSKI, J. MED. 19: 145–177, 1980).

This hypothesis is supported by the fact that Thapsigargin, as an indirect stimulator of the unselective cation channels (UCC) not only leads to a $Ca^{2+}$-overload in the cell but is also a highly effective tumour promoter. (V. THASTRUP et al. Proceedings of the NATL. Acad. Sci: (USA) 87: 2466–2470, 1990).

The blockade of the $Ca^{2+}$-influx by the UCC leads to normalisation of the intracellular Ca-ion concentration and hence to inhibition of tumour growth etc.

Conventional calcium antagonists do not inhibit these UCC. It has been found, surprisingly, that the compounds according to this invention inhibit the influx of calcium into the cell through the UCC.

As shown by S. H. MURCH et al. (Lancet 339 : 381–385, 15. Feb. 1992) endothelin I plays an important pathophysiological role in inflammatory intestinal diseases such as ulcerative colitis and Crohn's disease. Using immunohistochemical methods it has been shown that patients with Crohn's disease in the region of the submucosa and patients with ulcerative colitis in the region of the lamina propria of the epithelium of the large intestine show significantly and greatly increased concentrations of endothelin I compared with healthy normal people. It is assumed that the local secretion of endothelin causes massive vasospasms with consecutive disseminated ischaemia with microinfarcts which are regarded as the actual cause of the above diseases. The vasospasmogenic effectiveness of endothelin is explained by a $Ca^{2+}$-overload of vascular myocytes. Endothelin primarily triggers an $IP_3$-mediated intracellular release of $Ca^{2+}$ which is followed by a massive transmembranal $Ca^{2+}$-entry through dihydropyridine-insensitive channels. (M. S. Simonson et al. Clin. Invest. Med. 14: 499–507, 1991; T. Masakai, J. Cardiovasc. Pharmacol. 13:Suppl. 5, S1–S4, 1989; D. W. Hay, R. J. Pharmacol. 100: 383–392, 990). These channels are unselective cation channels which have also been briefly described as existing in cells of the large intestine mucosa. (Chr. Siemer and H. Gögelein, Europ. J. Physiol. 420: 319–328, 1992).

The endothelin-stimulated activation of fura-2-charged human leukaemia cells (HL 60 cells) has proved a suitable screening model for detecting functional endothelin antagonists. In conformity with G. GRYNKIEWICZ et al. (J. Biol. Chem. 260:3440–3450, 1985) the intracellular $Ca^{2+}$-concentration in the cytoplasm of HL 60 cells (suspensions) can be monitored by spectrofluorometry and quantified as a measurement of cell activation by endothelin. The stimulation was effected by adding 0.1 µM endothelin and could be inhibited in a dosage-dependent manner by means of the substances according to the invention.

The functional endothelin antagonism of the substances according to the invention is mediated through a blockade of the unselective cation channels. Consequently, detection of a functional Thapsigarginantagonism on RBL-hml cells is also a suitable screening method for functional endothelin antagonists.

Carrying out the investigation:

For screening purposes, fura-2-charged adhesive RBL-hm 1 cells are stimulated with 0.1 µM Thapsigargin in a $Ca^{2+}$-free free incubation medium. After 4 minutes, extracellular $Ca^{2+}$ is restored to a concentration of 1.5 mM and, using the fura-2-fluorescence, the excessive increase in the cytoplasmic $Ca^{2+}$-concentration caused by a massive transmembranal $Ca^{2+}$-entry through unselective cation channels is recorded.

This entry is to be inhibited solely by unselective cation channel blockers in a dosage-dependent manner. Neither conventional calcium antagonists nor specific blockers of agonists which stimulate the $IP_3$-turnover are able to inhibit the transmembranal $Ca^{2+}$-entry triggered indirectly by Thapsigargin. The compounds of the present invention are distinguished by their inhibktion of UCC.

The fluorometric calcium measurement in the cytoplasm of individual adhering RBL-hml cells is carried out analogously to the method described by KUDO and OGURA (1986) for neuronal cells. An AXIOVERT 35 fluorescence microscope made by ZEISS is used in conjunction with an imaging system made by HAMAMATSU, consisting of the ICMS-image processing system, residual light camera with control unit and image intensifier DVS 3000.

The kinetics of the cytoplasmic $Ca^{2+}$-concentration is recorded continuously as a concentration/time curve after the cell activation stimulated by Thapsigargin (0.1 µM). The curves of two activated cell cultures are compared in the presence and absence of 10 µM test substance. The area under these curves (area under the curve=AUC) is integrated and recorded as a measurement of cell activation. The inhibitory potency of the UCC-blockers tested is determined using the following equation:

$$\% H = 100 - \frac{AUC_{inh} \times 100}{AUC_{(control)}}$$

%H=the percentage inhibition of the calcium entry through unselective cation channels which is stimulated and inhibited by 10 µM of test substance.

$AUC_{inh}$=area under the curve recorded in the presence of the stimulant plus 10 µM inhibitory test substance.

$AUC_{control}$=area under the curve which is recorded only after the addition of the stimulant.

Literature relating to the above explanations:

BARNES P. J., I. W. RODGER and N. C. THOMSON Pathogenesis of asthma, in "ASTHMA, basic mechanisms and clinical management"ED by P. J. BARNES; ACADEMIC PRESS, LONDON, 1988

GRYNKIEWICZ G., M. POENIE and R. Y. TSIEN A new generation of $Ca^{2+}$-indicators with greatly improved fluorescence properties J. BIOL. CHEM. 260: 3440–3450, 1985

HIDE, M. and M. A. BEAVEN Calcium influx in a rat mast cell (RBL-2H3) life J. BIOL. CHEM. 266 15221–15229, 1991

KUDO, Y. and A. OGURA Glutamate-induced increase in intracellular $Ca^{2+}$-concentration in isolated hippocampal neurones BR. J. PHARMACOL. 89: 191–198, 1986

PUTNEY, J. W., jr. Capacitative Calcium entry revised CELL CALCIUM 11: 611–624, 1990

RINK, T. J. Receptor-mediated calcium entry FEBS LETT. 268: 381–385, 1990

SEIFERT, R. and G. SCHULTZ The superoxide forming NADPH oxidase of phagocytes: An enzyme system regulated by multiple mechanism REV. PHYSIOL. BIOCHEM. PHARMACOL., Vol. 117, SPRINGER VERL., 1991

WELLS, E., C. G. JACKSON, S. T. HARPER, J. MANN and R. P. EAOY Characterization of primate bronchoalveolar mast cells II, inhibition of histamine, $LTC_4$ and $PGF_{2\alpha}$ release from primate bronchoalveolar mast cells and a comparison with rat peritoneal mast cells J. IMMUNOL. 137: 3941–3945, 1986.

Results of measurement:

The percentage inhibition of UCC after Thapsigargin stimulation (0.1 µM Thapsigargin) in RBL-hm 1 cells is given. The uniform concentration of the test substances is $10^{-5}$ mol).

TABLE 21

(Data relating to compounds of Tables 1–10)
RBL - hm 1 cells - Thapsigargin (0.1 µM) stimulation

| Compound No. | % Inhibition |
|---|---|
| 3 | F 41.91 |
| 4 | F 66.53 |
| 5 | F 80.16 |
| 9 | F 67.59 |
| 14 | F 80.16 |
| 17 | F 52.53 |
| 18 | F 57.53 |
| 20 | F 57.38 |
| 33 | 60.55 |
| 36 | F 52.19 |

TABLE 21-continued (Data relating to compounds of Tables 1–10)
RBL - hm 1 cells - Thapsigargin (0.1 µM) stimulation

| Compound No. | % Inhibition |
|---|---|
| 37 | F 75.77 |
| 38a (oxalate) | 52.64 |
| 39 | 48.62 |
| 40 | 64.99 |
| 41 (Structure I) | F 57.22 |
| 42 | 84.83 |
| 43 | F 48.69 |
| 46 | 68.06 |
| 48 | 61.34 |
| 83 | 66.76 |
| 89 | 53.38 |
| B | 72.35 |
| C | 63.45 |
| E | F 81.89 |
| F | 48.01 |
| G | 57.52 |
| H | 57.06 |
| K | 76.31 |
| L | 53.14 |
| O | 63.32 |
| Q | 64.28 |
| 101 | 59.62 |
| 102 | F 80.77 |
| 104 | 54.67 |
| 105 | 45.09 |
| 106 | F 65.69 |
| 108 | 44.45 |
| 109 | 74.18 |
| 115 | 75.53 |
| 132 | F 65.14 |
| 133 | 68.15 |

The activity data (%inhibition and $IC_{50}$) for other compounds are contained in Tables 13–20.

The functional antiinflammatory effectiveness can be demonstrated by means of the following test:

Individual RBL-2H3-cells (a tumour cell line related to the mast cells) adhering to glass slides are used.

The cultivation and attachment of the RBL-2H3-cells are carried out by the method described by HIDE and BEAVEN (1991). In order to sensitise the adhesive RBL-2H3-cells the cells are incubated for 2 hours at ambient temperature with a 1:2000 diluted commercial gammaglobulin E-solution against a dinitrophenol-bovine serum albumin complex (DNP-BSA-antigen). The cells are then washed. By the addition of 0.1 ml of DNP-BSA-solution (10 µg/ml) there is a massive immunological cell activation which is mediated by a cytoplasmic $Ca^{2+}$-overload. The fluorometric calcium measurement in the cytoplasm of individual adhering RBL-2H3-cells is carried out analogously to the method described by KUDO and OGURA (1986) for neuronal cells, which is also explained hereinbefore in this specification.

The comparison used in these investigations is (~10 µM) chromoglycate which brings about an approximately 50% inhibition of the antigen-induced cell activation.

In this test the above-mentioned compounds demonstrate % H values which are comparable with the values specified hereinbefore.

Tests on microcultures of various human tumour cell lines using the tetrazolium assay in order to determine the antiproliferative effect of the substances according to the invention surprisingly showed that the compound tested was 5 to 100 times more potent than the comparison substance Verapamil.

The antiproliferative effectiveness of the test substances was determined by means of the MTT test described by MOSMANN (J. IMMUNOL. METH. 65: 55–63, 1983), DENIZOT et al. (J. IMMUNOL. METH. 89: 271–277, 1986) and J. ELIASON et al. (INT. J. CANCER 46: 113–117, 1990). (MTT=[3-(4,5-dimethylthiazol-2-yl)2,5-diphenyl-tetrazolium bromide] produced by CHEMICON Inc. El Segundo, Calif., U.S.A.). This indicator is metabolised only by living cells with intact mitochondria into a blue formazane product. The following human tumour cell lines were used in our test: A 549 (adenocarcinoma of the lung), A 431 (epidermal carcinoma of the vulva), PC 3 (adenocarcinoma of the prostate), SK BR 3 (adenocarcinoma of the breast), HT 29 (CX1 1) (adenocarcinoma of the colon) and K 562 (chronic myeloid leukaemia cell). The test was carried out on microtitre plates. Each well contained 100 µl of a cell suspension ($0.2 \times 10^6$ cells per ml). The incubation medium used was RPMI 1640 with 10% heat-inactivated foetal calves' serum and 50 µg/ml of gentamycin. The cell suspensions were incubated for 0, 24, 48 or 72 hours in air with a humidity at saturation point in a $CO_2$ (5%)/air (95%) mixture at 37° C., incubated in the presence and absence of variable concentrations of antiproliferative test substances. The test substances were dissolved in DMSO (final dilution: 0.1%). Then 10 µl of MTT-solution (3 mg/ml) were added, followed after 3 hours by 100 µl of an isopropanol solution containing 0.08 N HCl. After a further hour, the light absorption at 570 nm (comparative wavelength 630 nm) was determined in a microplate reader. The light absorption is directly proportional to the number of living cells. The half-maximum inhibitory concentrations of the substances tested were 1 µg/ml.

The vasospasmolytic effectiveness of the above-mentioned functional endothelin and Thapsigargin antagonists were confirmed on an isolated blood vessel preparation: coronary perfusion was continuously quantified, on retrogressively perfused, spontaneously beating LANGENDORFF hearts taken from rats, by means of electromagnetic flow measurement (apparatus supplied by Hugo Sachs Elektronik, MARCH). This measuring apparatus could be used to record the extent, duration and pattern of vascular spasms with a high degree of accuracy. If perfusion is carried out with 100 nM endothelin concentration, the coronary perfusion flow is reduced from 11 to 5 ml/min. The restriction in perfusion can be reversed by means of the substances according to the invention. The potencies of the compounds according to the invention with regard to Thapsigargin inhibition on fura-2-charged RBL-hml-cells or the effectiveness of endothelin-inhibition on fura-2-charged HL 60 cells correlates clearly with the vasospasmolytic effectiveness of the test substances detected on the Langendorff preparation. It can be concluded from this that, underlying the vasospasmolytic endothelin antagonism of the substances tested, there is a blockade of the unselective cation channels.

Examples of Pharmaceutical Preparations

| a) Coated tablets | |
|---|---|
| 1 tablet core contains: | |
| Active substance of general formula I | 30.0 mg |
| Lactose | 100.0 mg |
| Corn starch | 75.0 mg |
| Gelatine | 3.0 mg |
| Magnesium stearate | 2.0 mg |
| | 210.0 mg |

Preparation

The active substance mixed with lactose and corn starch is granulated with a 10% aqueous gelatine solution through a 1 mm mesh screen, dried at 40° C. and rubbed through a screen once more. The granules thus obtained are mixed with magnesium stearate and compressed. The cores produced in this way are coated in the usual manner with a coating consisting of an aqueous suspension of sugar, titanium dioxide, talc and gum arabic. The finished coated tablets are polished with beeswax.

| b) Tablets | |
|---|---|
| Active substance of general formula I | 30.0 mg |
| Lactose | 100.0 mg |
| Corn starch | 70.0 mg |
| Soluble starch | 7.0 mg |
| Magnesium stearate | 3.0 mg |
| | 210.0 mg |

Preparation

The active substance and magnesium stearate are granulated with an aqueous solution of the soluble starch, the granules are dried and intimately mixed with lactose and corn starch. The mixture is then compressed into tablets weighing 210 mg.

| c) Capsules | |
|---|---|
| Active substance according to claim 1 | 20.0 mg |
| Lactose | 230.0 mg |
| Corn starch | 40.0 mg |
| Talc | 10.0 mg |
| | 300.0 mg |

Preparation

The active substance, lactose and corn starch are first combined in a mixer and then in a grinding machine. The mixture is returned to the mixer, thoroughly combined with the talc and mechanically packed into hard gelatine capsules.

| d) Tablets | |
|---|---|
| Active substance according to the invention | 40.0 mg |
| Lactose | 100.0 mg |
| Corn starch | 50.0 mg |
| Colloidal silica | 2.0 mg |
| Magnesium stearate | 3.0 mg |
| Total | 200.0 mg |

Preparation

The active substance is mixed with some of the excipients and granulated with a solution of the soluble starch in water. After the granules have been dried the remaining excipients are added and the mixture is compressed to form tablets.

| e) Coated tablets | |
|---|---|
| Active substance according to the invention | 20.0 mg |
| Lactose | 100.0 mg |
| Corn starch | 65.0 mg |
| Colloidal silica | 2.0 mg |

| e) Coated tablets | |
|---|---|
| Soluble starch | 5.0 mg |
| Magnesium stearate | 3.0 mg |
| Total | 195.0 mg |

Preparation

The active substance and excipients are compressed to form tablet cores as described in Example 1 which are then coated with sugar, talc and gum arabic in the usual way.

| f) Suppositories | |
|---|---|
| Active substance according to the invention | 50.0 mg |
| Lactose | 250.0 mg |
| Suppository mass q.s. ad | 1.7 g |

Preparation

The active substance and lactose are mixed together and the mixture is uniformly suspended in the molten suppository mass. The suspensions are poured into cooled moulds to form suppositories weighing 1.7 g.

| g) Ampoules | |
|---|---|
| Active substance according to the invention | 20.0 mg |
| Sodium chloride | 5.0 mg |
| Twice distilled water q.s. ad | 2.0 ml |

Preparation

The active substance and sodium chloride are dissolved in twice distilled water and the solution is transferred under sterile conditions into ampoules.

| h) Ampoules | |
|---|---|
| Active substance according to the invention | 10.0 mg |
| Sodium chloride | 7.0 mg |
| Twice distilled water q.s. ad | 1.0 mg |

| i) Drops | |
|---|---|
| Active substance according to the invention | 0.70 g |
| Methyl p-hydroxybenzoate | 0.07 g |
| Propyl p-hydroxybenzoate | 0.03 g |
| Demineralised water q.s. ad | 100.00 ml |

Preparation

The active substance and preservatives are dissolved in demineralised water, the solution is filtered and transferred into vials holding 100 ml.

What is claimed is:
1. A compound of formula

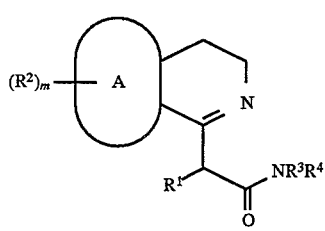

wherein

A is a benzo;

m is 2;

R² are in positions 6 and 7 and independently of each other may be hydroxy, ($C_{1-4}$)alkoxy, benzyloxy, halogen, ($C_{1-4}$)alkyl, methanesulphonyloxy or methanesulphonamido or two adjacent substituents R² together may be —O—CH₂—O or —O—CH₂—CH₂—O—;

R¹ is ($C_{4-6}$)cyloalkyl or ($C_{4-6}$)cycloalkyl($C_{1-5}$)-alkyl;

R³ and R⁴ independently or each other are
(a) hydrogen,
(b) branched or unbranched $C_{3-6}$-alkenyl,
(c) branched or unbranched $C_{3-6}$-alkynyl,
(d) branched or unbranched $C_{1-12}$-alkyl, whilst the alkyl may be substituted by
hydroxy,
($C_{1-4}$)alkoxy,
di($C_{1-4}$)akylamino,
furyl,
pyridyl,
pyrrolidinyl, N-methylpyrrolidinyl,
morpholino,
indolyl,
nitrilo,
thienyl,
adamantyl,
cyclohexyl,
phenoxy,
napthyloxy or phenyl, whilst this phenyl or the phenyl contained in the phenoxy group may be mono-, di- or trisubstituted by hydroxy, ($C_{1-4}$) alkoxy, benzyloxy, halogen, $CF_3$, $N_3$, ($C_{1-4}$)alkyl, adamantyl, —$SO_2NH_2$ or by the bridge —O—CH₂—O—;

or R³ is hydrogen and R⁴ is cyclohexyl, phenyl, fluorophenyl, pyridyl or N-benzylpiperidyl;

or R³ and R⁴ together with the nitrogen atom to which they are bound represent
pyrrolidinyl,
piperidinyl,
morpholino, thiomorpholino, the group

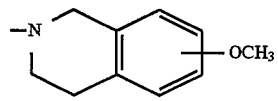

or piperazinyl, whilst the piperazinyl ring may optionally be N-substituted by methyl, unsubstituted phenyl, mono- or di($C_{1-4}$)alkoxyphenyl, pyrimidinyl, phenyl($C_{1-4}$)alkyl or

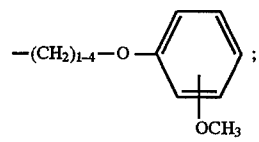

or the salts thereof with physiologically acceptable acids, bases or complexing agents.

2. The compounds as recited in claim 1, wherein R¹ is cyclohexyl, cyclohexylmethylene or cyclobutylmethylene.

3. The compounds as recited in claim 2 wherein NR³R⁴ is

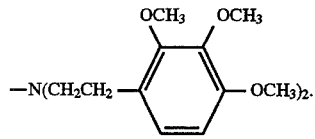

4. The compounds as recited in claim 1 of formula

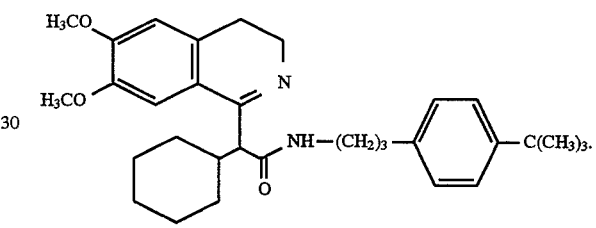

5. The compounds as recited in claim 1 wherein NR³R⁴ is

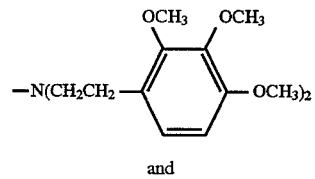

and

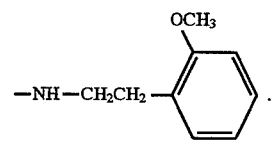

6. A method for treating chronic inflammatory processes, ulcerative colitis and Crohn's disease in a warm-blooded animal, which comprises administering to said animal a therapeutically effective amount of the compound of claim 1.

7. A method for treating diseases in a warm-blooded animal that responds to an agent with antiproliferative activity which comprises administering to said animal a therapeutically effective amount of the compound of claim 1.

* * * * *